United States Patent
Jung et al.

(10) Patent No.: US 10,323,006 B2
(45) Date of Patent: Jun. 18, 2019

(54) HETEROCYCLIC COMPOUND AND ORGANIC LIGHT EMITTING ELEMENT USING SAME

(71) Applicant: LG Chem, Ltd., Seoul (KR)

(72) Inventors: Min Woo Jung, Daejeon (KR); Dong Hoon Lee, Daejeon (KR); Jungoh Huh, Daejeon (KR); Boonjae Jang, Daejeon (KR); Minyoung Kang, Daejeon (KR); Dong Uk Heo, Daejeon (KR); Miyeon Han, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/757,078

(22) PCT Filed: Sep. 8, 2016

(86) PCT No.: PCT/KR2016/010090
§ 371 (c)(1),
(2) Date: Mar. 2, 2018

(87) PCT Pub. No.: WO2017/043886
PCT Pub. Date: Mar. 16, 2017

(65) Prior Publication Data
US 2018/0244630 A1    Aug. 30, 2018

(30) Foreign Application Priority Data

Sep. 11, 2015 (KR) .................. 10-2015-0129129
Jul. 26, 2016 (KR) .................. 10-2016-0094992

(51) Int. Cl.
| C07D 239/24 | (2006.01) |
| C07D 251/12 | (2006.01) |
| C07D 401/14 | (2006.01) |
| C07D 403/14 | (2006.01) |
| C09K 11/06 | (2006.01) |
| H01L 51/50 | (2006.01) |

(52) U.S. Cl.
CPC ......... *C07D 239/24* (2013.01); *C07D 251/12* (2013.01); *C07D 401/14* (2013.01); *C07D 403/14* (2013.01); *C09K 11/06* (2013.01); *H01L 51/50* (2013.01); *H01L 51/5056* (2013.01)

(58) Field of Classification Search
None
See application file for complete search history.

(56) References Cited

U.S. PATENT DOCUMENTS

| 9,120,773 B2 | 9/2015 | Aihara et al. |
| 2007/0190355 A1 | 8/2007 | Ikeda et al. |
| 2010/0249406 A1 | 9/2010 | Yamakawa et al. |
| 2014/0299192 A1 | 10/2014 | Lee et al. |
| 2016/0233430 A1 | 8/2016 | Heo et al. |

FOREIGN PATENT DOCUMENTS

| EP | 1724323 A1 | 11/2006 |
| JP | 2000044519 A | 2/2000 |
| JP | 2014103103 A | 6/2014 |
| JP | 2014141467 A | 8/2014 |
| JP | 2015524797 A | 8/2015 |
| KR | 20090008737 A | 1/2009 |
| KR | 20090130008 | 12/2009 |
| KR | 20110041727 A | 4/2011 |
| KR | 20120036560 A | 4/2012 |
| KR | 20130135162 A | 12/2013 |
| KR | 20140087804 A | 7/2014 |
| KR | 20140094408 A | 7/2014 |
| KR | 20150010016 A | 1/2015 |
| KR | 20160090262 A | 7/2016 |
| WO | 2005085387 A1 | 9/2005 |
| WO | 2014057873 A1 | 4/2014 |
| WO | 2015046835 A1 | 4/2015 |

OTHER PUBLICATIONS

Search report from International Application No. PCT/KR2016/010090, dated Dec. 14, 2016.
Partial Supplementary European Search Report including Written Opinion for Application No. EP16844702.7 dated Jul. 6, 2018.
Extended European Search Report including Written Opinion for Application No. EP16844702.7 dated Sep. 27, 2018.

*Primary Examiner* — Alicia L Otton
(74) *Attorney, Agent, or Firm* — Lerner, David, Littenberg, Krumholz & Mentlik, LLP

(57) ABSTRACT

The present specification provides a heterocyclic compound and an organic light emitting device using the same.

18 Claims, 1 Drawing Sheet

[Figure 1]
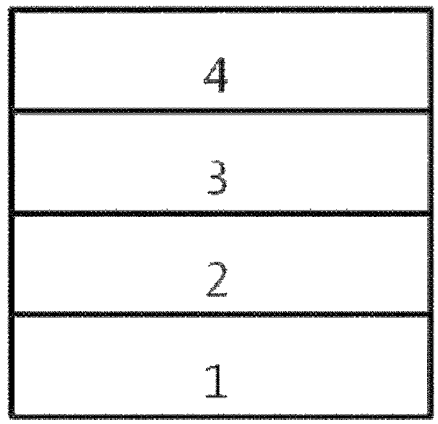
[Figure 2]
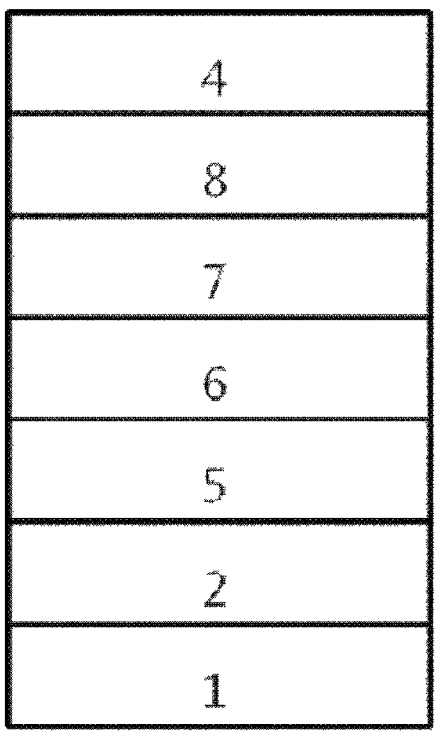

HETEROCYCLIC COMPOUND AND ORGANIC LIGHT EMITTING ELEMENT USING SAME

CROSS-REFERENCE TO RELATED APPLICATIONS

The present application is a national phase entry under 35 U.S.C. 371 of International Application No. PCT/KR2016/010090 filed on Sep. 8, 2016, which claims priority from Korean Patent Application Nos. 10-2015-0129129 and 10-2016-0094992 filed in the Korean Intellectual Property Office on Sep. 11, 2015 and Jul. 26, 2016, respectively, the entire contents of which are incorporated herein by reference.

TECHNICAL FIELD

The present specification relates to a heterocyclic compound and an organic light emitting device using the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present specification describes a heterocyclic compound and an organic light emitting device using the same.

Technical Solution

An exemplary embodiment of the present specification provides a compound represented by the following Chemical Formula 1.

[Chemical Formula 1]

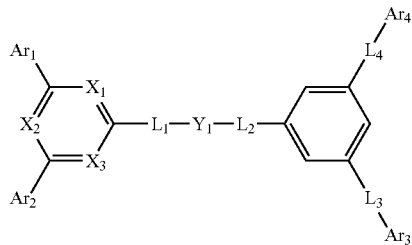

in Chemical Formula 1, $X_1$ to $X_3$ are the same as or different from each other, and are each independently N or $CR_1$, at least one of $X_1$ to $X_3$ is N, $R_1$ is hydrogen or deuterium, $Y_1$ is a substituted or unsubstituted naphthylene group, $L_1$ to $L_4$ are the same as or different from each other, and are each independently a direct bond; a substituted or unsubstituted arylene group; a substituted or unsubstituted heteroarylene group; or a substituted or unsubstituted divalent arylamine group, $Ar_1$ and $Ar_e$ are the same as or different from each other, and are each independently hydrogen; deuterium; a halogen group; an amino group; a nitrile group; a nitro group; a substituted or unsubstituted cycloalkyl group; a substituted or unsubstituted aryl group; or a substituted or unsubstituted heteroaryl group, and $Ar_3$ and $Ar_4$ are the same as or different from each other, and are each independently a substituted or unsubstituted pyridyl group.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material for hole injection, hole transport, hole injection and hole transport, electron inhibition, light emission, hole inhibition, electron transport, or electron injection.

In particular, an organic light emitting device having a longer lifetime may be obtained by using the compound as a material for an organic material layer of the organic light emitting device as compared to the case where the existing material is used.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4.

1: Substrate
2: Positive electrode
3, 7: Light emitting layer
4: Negative electrode
5: Hole injection layer
6: Hole transport layer
7: Light emitting layer
8: Electron transport layer

BEST MODE

Hereinafter, the present specification will be described in more detail.

An exemplary embodiment of the present specification provides the compound represented by Chemical Formula 1. Examples of the substituents will be described below, but are not limited thereto.

In the present specification,

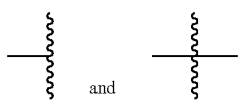

mean a moiety linked to another substituent.

In the present specification, the term "substituted or unsubstituted" means that a group is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or a substituent to which two or more substituents among the substituents exemplified above are linked is substituted or unsubstituted. For example, "the substituent to which two or more substituents are linked" may be a biphenyl group. That is, the biphenyl group may also be an aryl group, and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structures, but is not limited thereto.

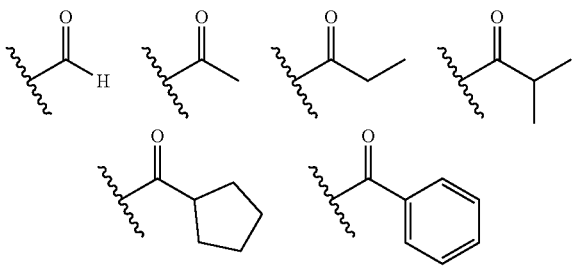

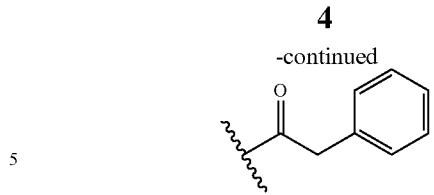

In the present specification, in an ester group, the oxygen of the ester group may be substituted with a straight-chained, branch-chained, or cyclic alkyl group having 1 to 40 carbon atoms, or an aryl group having 6 to 30 carbon atoms. Specifically, the ester group may be a compound having the following structural formulae, but is not limited thereto.

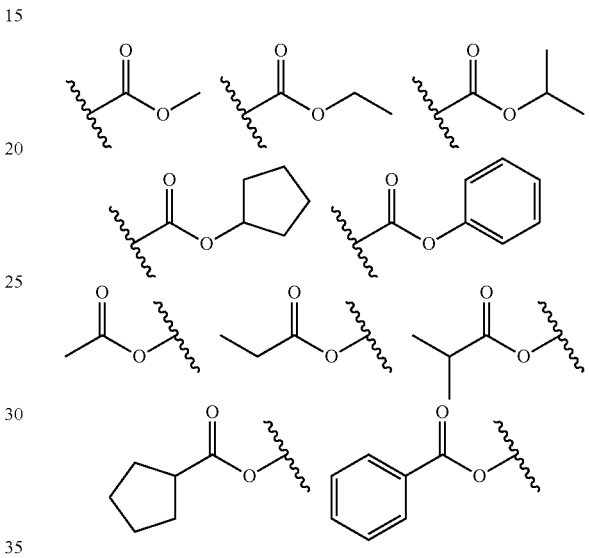

In the present specification, the number of carbon atoms of an imide group is not particularly limited, but is preferably 1 to 25. Specifically, the imide group may be a compound having the following structures, but is not limited thereto.

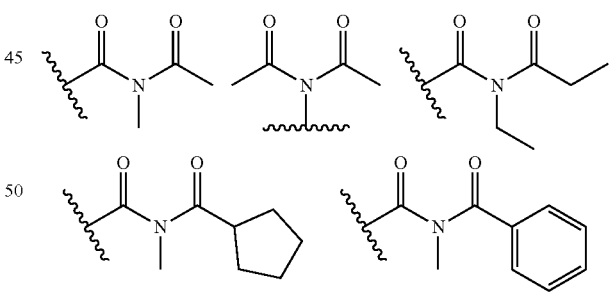

In the present specification, a silyl group may be represented by a chemical formula of $-SiR_aR_bR_c$, and $R_a$, $R_b$, and $R_c$ may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of $-BR_aR_b$, and $R_a$ and $R_b$ may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkoxy group may be straight-chained, branch-chained, or cyclic. The number of carbon atoms of the alkoxy group is not particularly limited, but is preferably 1 to 40. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

A substituent including an alkyl group, an alkoxy group, and other alkyl group moieties described in the present specification includes both a straight-chained form and a branch-chained form.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the number of carbon atoms of an alkylamine group is not particularly limited, but is preferably 1 to 40. Specific examples of the alkylamine group include a methylamine group, a dimethylamine group, an ethylamine group, a diethylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including the two or more aryl groups may include a monocyclic aryl group, a polycyclic aryl group, or both a monocyclic aryl group and a polycyclic aryl group.

Specific examples of the arylamine group include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, carbazole, a triphenylamine group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include a monocyclic heterocyclic group, a polycyclic heterocyclic group, or both a monocyclic heterocyclic group and a polycyclic heterocyclic group.

In the present specification, an arylheteroarylamine group means an amine group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the fluorenyl group may be a substituted fluorenyl group such as a spiro fluorenyl group such as

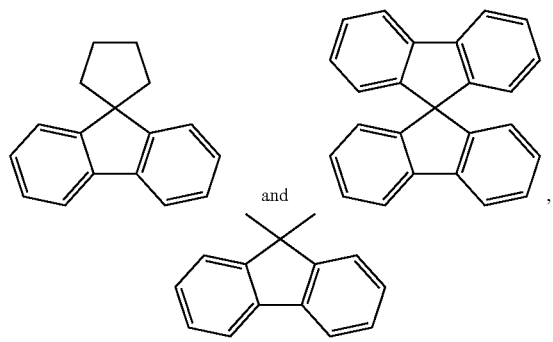

a 9,9-dimethylfluorenyl group), and

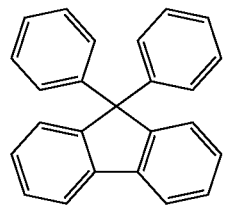 [SMILES: c1ccc(C2(c3ccccc3)c3ccccc3-c3ccccc32)cc1]

(a 9,9-diphenylfluorenyl group). However, the fluorenyl group is not limited thereto.

In the present specification, a heterocyclic group is a heterocyclic group including one or more of N, O, P, S, Si, and Se as a hetero atom, and the number of carbon atoms thereof is not particularly limited, but is preferably 1 to 60. According to an exemplary embodiment, the number of carbon atoms of the heterocyclic group is 2 to 30. Examples of the heterocyclic group include a pyridyl group, a pyrrole group, a pyrimidyl group, a pyridazinyl group, a furanyl group, a thiophenyl group, an imidazole group, a pyrazole group, an oxazole group, an isooxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acrydyl group, a xanthenyl group, a phenanthridinyl group, a diaza naphthalenyl group, a triazaindenyl group, an indole group, an indolinyl group, an indolizinyl group, a phthalazinyl group, a pyrido pyrimidinyl group, a pyrido pyrazinyl group, a pyrazino pyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzoimidazoquinazoline group, or a benzoimidazophenanthridine group, and the like, but are not limited thereto.

In the present specification, the above-described description on the heterocyclic group may be applied to a heteroaryl group except for an aromatic group.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the above-described description on the alkyl group may be applied to an alkyl group in an alkylthioxy group, an alkylsulfoxy group, an aralkyl group, an aralkylamine group, an alkylaryl group, and an alkylamine group.

In the present specification, the above-described description on the heterocyclic group may be applied to a heteroaryl group in a heteroaryl group, a heteroarylamine group, and an arylheteroarylamine group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

According to an exemplary embodiment of the present specification, the compound represented by Chemical Formula 1 may be represented by the following Chemical Formula 2.

[Chemical Formula 2]

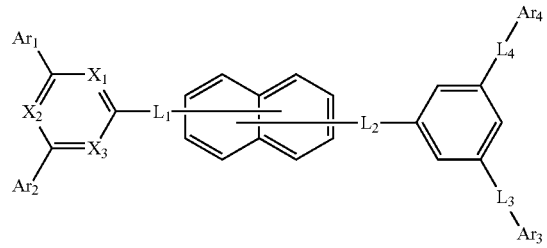

In Chemical Formula 2, the definitions of $X_1$ to $X_3$, $Ar_1$ to $Ar_4$, and $L_1$ to $L_4$ are the same as those in Chemical Formula 1.

In an exemplary embodiment of the present invention, $L_1$ to $L_4$ are the same as or different from each other, and are each independently a direct bond; or a substituted or unsubstituted arylene group.

In an exemplary embodiment, $L_1$ to $L_4$ are all a direct bond.

In an exemplary embodiment, $L_1$ and $L_3$ are a direct bond, and $L_2$ and $L_4$ are a substituted or unsubstituted arylene group.

In an exemplary embodiment, $L_1$ and $L_3$ are a substituted or unsubstituted arylene group, and $L_2$ and $L_4$ are a direct bond.

In an exemplary embodiment, $L_1$ to $L_4$ are all a substituted or unsubstituted arylene group.

Further, in the present specification, L₁ to L₄ are the same as or different from each other, and are each independently preferably any one substituent selected from the following group, but are not limited thereto, and the following structures may be additionally substituted.

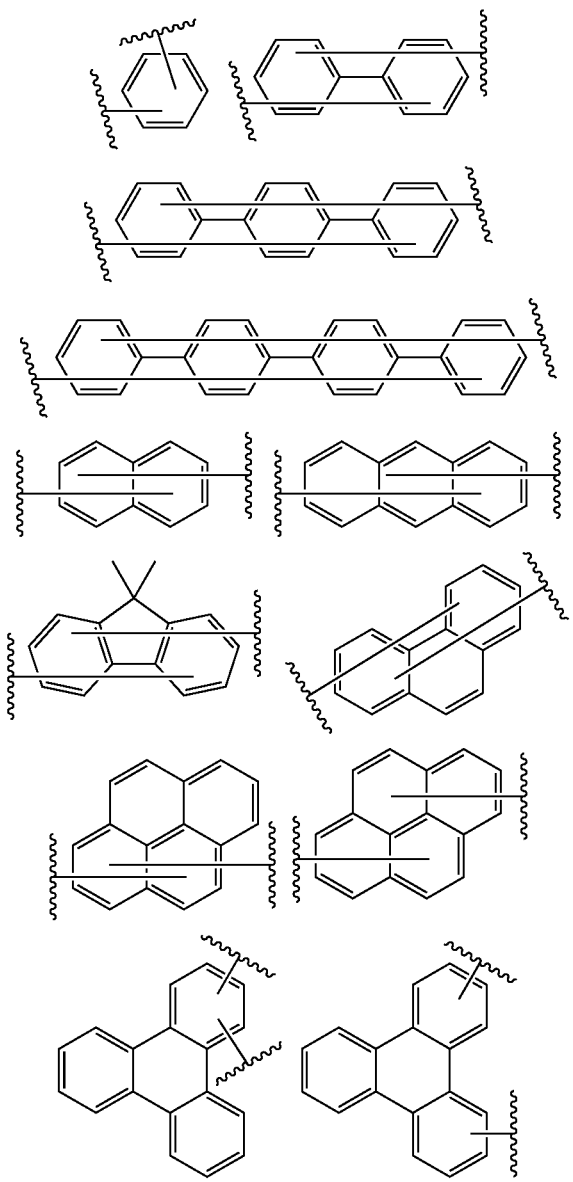

The structures may be unsubstituted or substituted with one or more substituents selected from the group consisting of deuterium; a halogen group; a nitrile group; a nitro group; a hydroxy group; a carbonyl group; an ester group; an imide group; an amine group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

In another exemplary embodiment, $L_1$ to $L_4$ are the same as or different from each other, and are each independently a direct bond; or a substituted or unsubstituted phenylene group.

In an exemplary embodiment, $L_1$ and $L_2$ are all a direct bond.

In an exemplary embodiment, $L_1$ and $L_2$ are different from each other, one of $L_1$ and $L_2$ is a direct bond, and the other is a substituted or unsubstituted phenylene group.

In an exemplary embodiment, $L_1$ and $L_2$ are all a substituted or unsubstituted phenylene group.

In an exemplary embodiment, $L_3$ and $L_4$ are all a direct bond.

In an exemplary embodiment, $L_3$ and $L_4$ are different from each other, one of $L_3$ and $L_4$ is a direct bond, and the other is a phenylene group.

In an exemplary embodiment, $L_3$ and $L_4$ are all a substituted or unsubstituted phenylene group.

According to an exemplary embodiment of the present specification, the compound represented by Chemical Formula 1 may be represented by the following Chemical Formula 3 or 4.

[Chemical Formula 3]

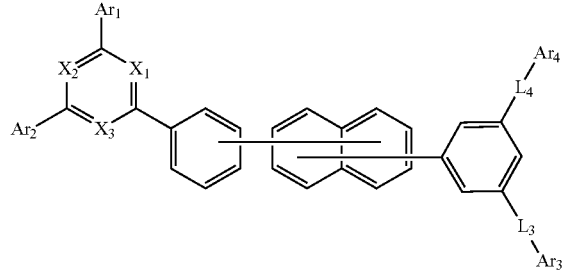

[Chemical Formula 4]

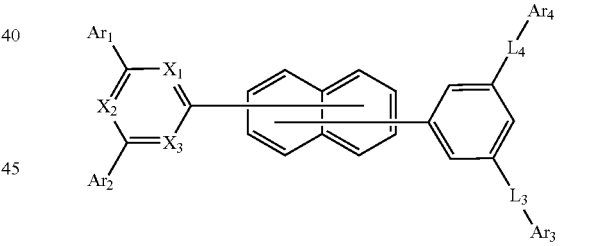

In Chemical Formulae 3 and 4, the definitions of $X_1$ to $X_3$, $Ar_1$ to $Ar_4$, $L_3$, and $L_4$ are the same as those in Chemical Formula 1.

In an exemplary embodiment, $Y_1$ is a substituted or unsubstituted naphthylene group.

In an exemplary embodiment of the present invention, $Y_1$ is any one selected from the following structures.

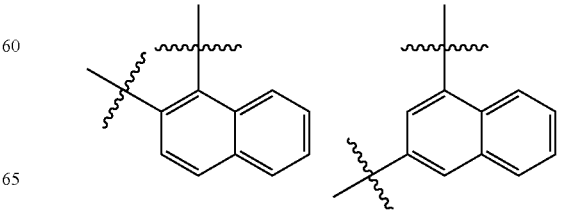

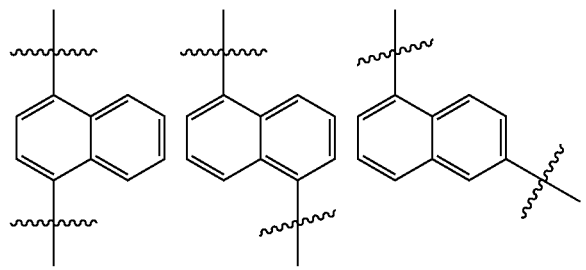
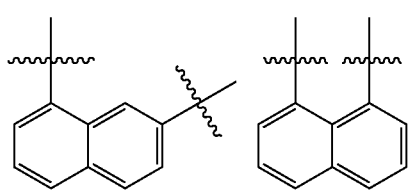
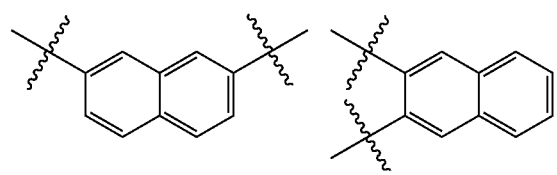
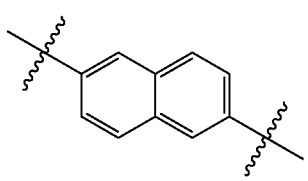
According to an exemplary embodiment of the present specification, the compound represented by Chemical Formula 1 may be represented by the following Chemical Formulae 5 to 14.
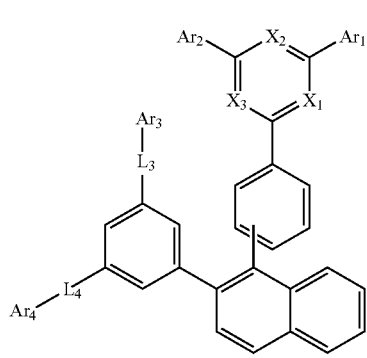
[Chemical Formula 5]
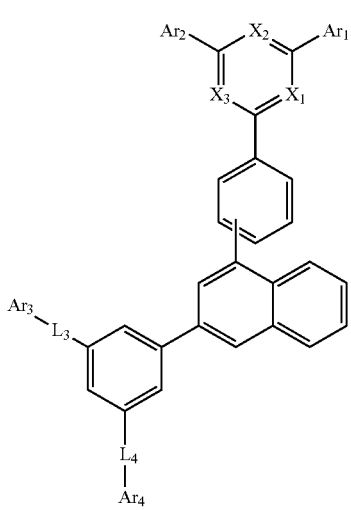
[Chemical Formula 6]
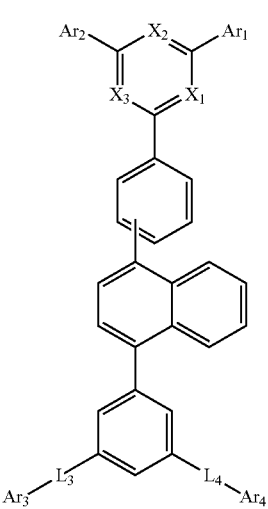
[Chemical Formula 7]
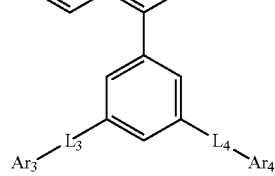
[Chemical Formula 8]

[Chemical Formula 9]

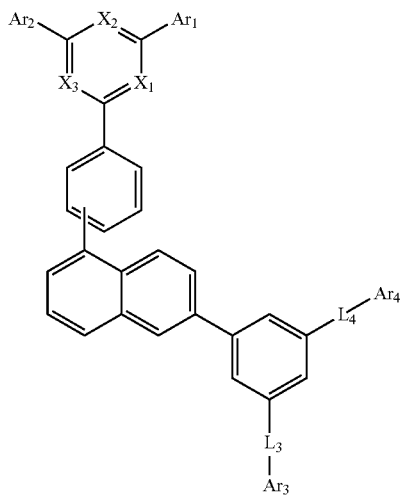

[Chemical Formula 10]

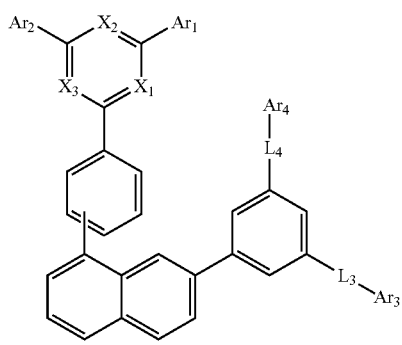

[Chemical Formula 11]

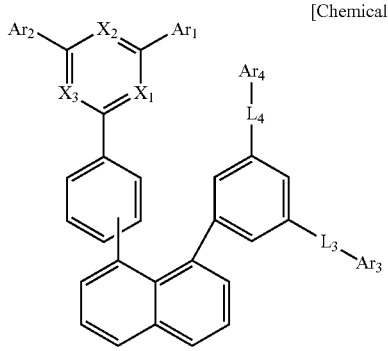

[Chemical Formula 12]

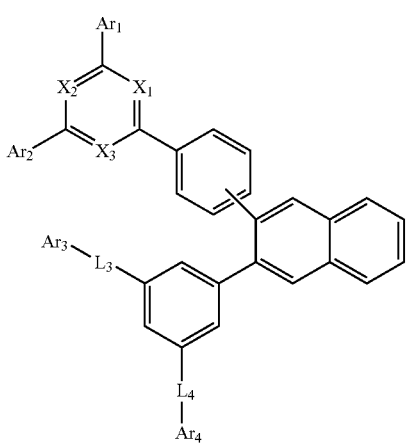

[Chemical Formula 13]

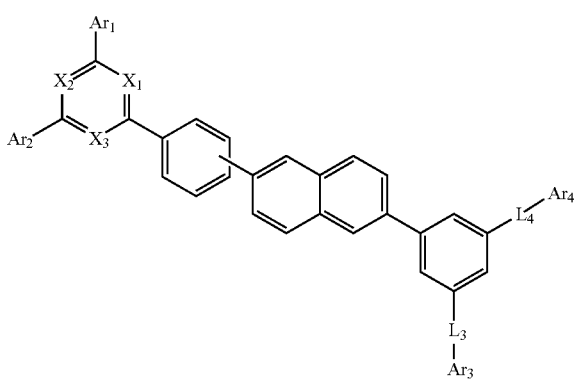

[Chemical Formula 14]

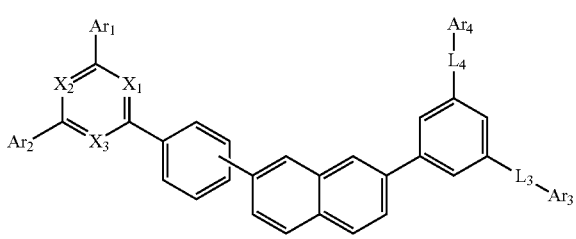

In Chemical Formulae 5 to 14, the definitions of $X_1$ to $X_3$, $Ar_1$ to $Ar_4$, $L_3$, and $L_4$ are the same as those in Chemical Formula 1.

According to an exemplary embodiment of the present specification, the compound represented by Chemical Formula 1 may be represented by the following Chemical Formulae 15 to 24.

[Chemical Formula 15]
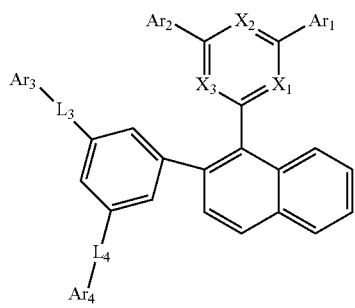
[Chemical Formula 16]
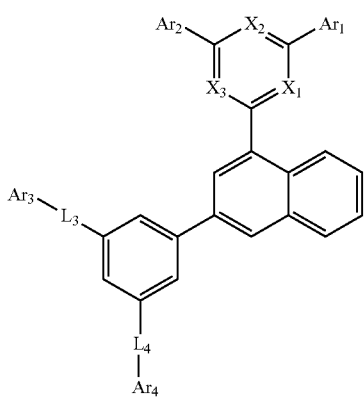
[Chemical Formula 17]
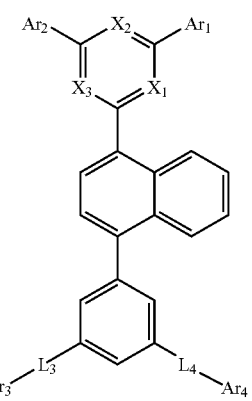
[Chemical Formula 18]
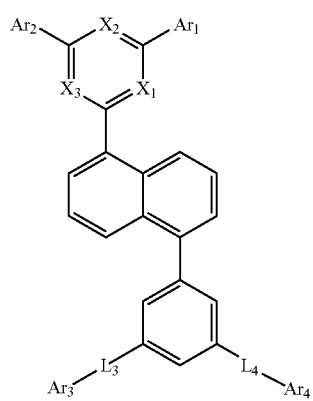
[Chemical Formula 19]
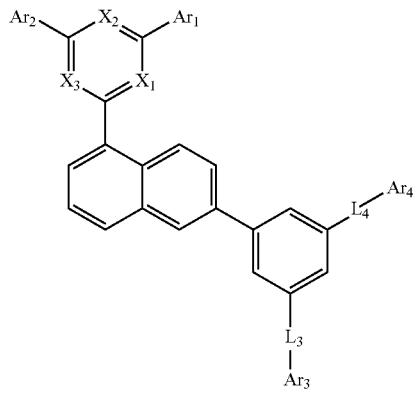
[Chemical Formula 20]
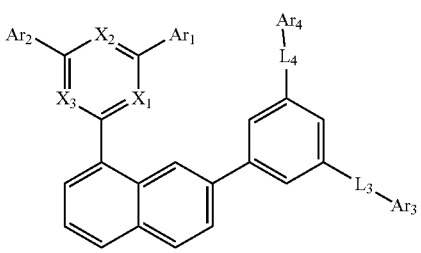
[Chemical Formula 21]
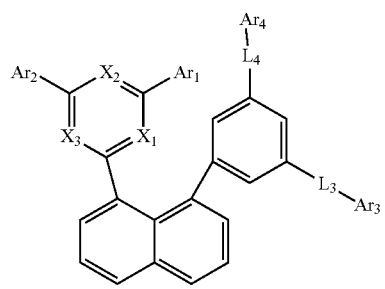
[Chemical Formula 22]
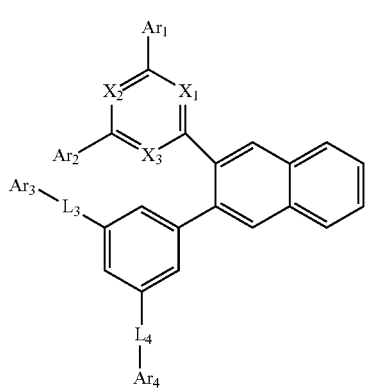

[Chemical Formula 23]

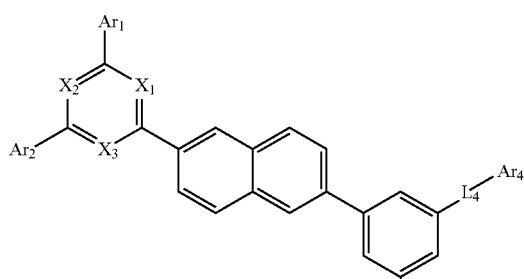

[Chemical Formula 24]

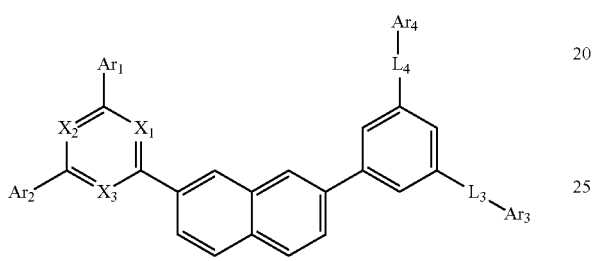

In Chemical Formulae 15 to 24, the definitions of $X_1$ to $X_3$, $Ar_1$ to $Ar_4$, $L_3$, and $L_4$ are the same as those in Chemical Formula 1.

In an exemplary embodiment of the present invention, $Ar_1$ and $Ar_2$ are the same as or different from each other, and are each independently hydrogen; deuterium; a halogen group; an amino group; a nitrile group; a nitro group; a substituted or unsubstituted cycloalkyl group; a substituted or unsubstituted aryl group; or a substituted or unsubstituted heteroaryl group.

In an exemplary embodiment of the present invention, $Ar_1$ and $Ar_2$ are the same as or different from each other, and are each independently hydrogen; deuterium; a substituted or unsubstituted aryl group having 6 to 60 carbon atoms; or a substituted or unsubstituted heteroaryl group having 1 to 60 carbon atoms.

In an exemplary embodiment of the present invention, $Ar_1$ and $Ar_2$ are the same as or different from each other, and are each independently hydrogen; deuterium; or a substituted or unsubstituted monocyclic or polycyclic aryl group having 6 to 30 carbon atoms.

In an exemplary embodiment, $Ar_1$ and $Ar_2$ are the same as or different from each other, and are each independently hydrogen; deuterium; a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthryl group; a substituted or unsubstituted pyrenyl group; a substituted or unsubstituted perylenyl group; a substituted or unsubstituted chrysenyl group; or a substituted or unsubstituted fluorenyl group.

In an exemplary embodiment, $Ar_1$ and $Ar_2$ are the same as or different from each other, and are each hydrogen; or a substituted or unsubstituted phenyl group.

In an exemplary embodiment, $Ar_1$ and $Ar_e$ are all a substituted or unsubstituted phenyl group.

According to an exemplary embodiment of the present specification, $Ar_3$ and $Ar_4$ are the same as or different from each other, and are each independently a substituted or unsubstituted pyridyl group.

According to an exemplary embodiment of the present specification, $Ar_3$ and $Ar_4$ are the same as or different from each other, and are each independently

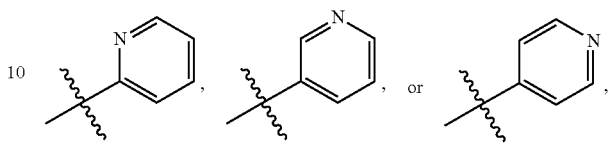

In an exemplary embodiment of the present invention, the compound of Chemical Formula 1 may be any one selected from the following compounds.

[Compound 1]

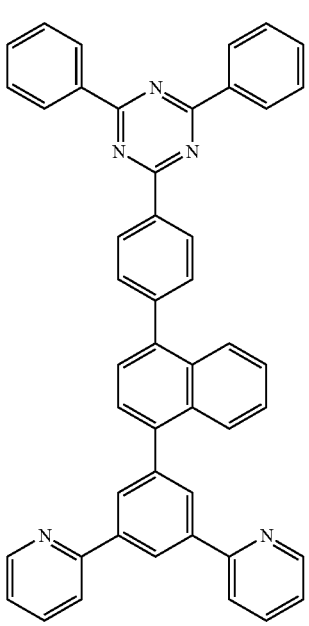

[Compound 2]

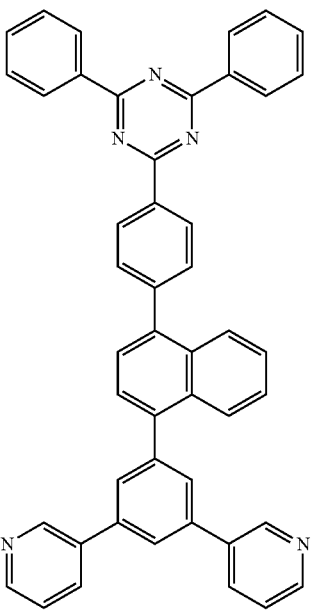

[Compound 3]
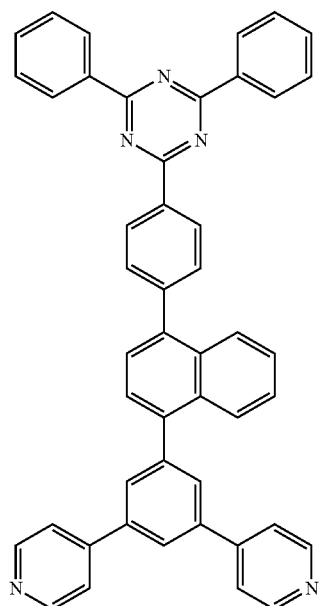
[Compound 5]
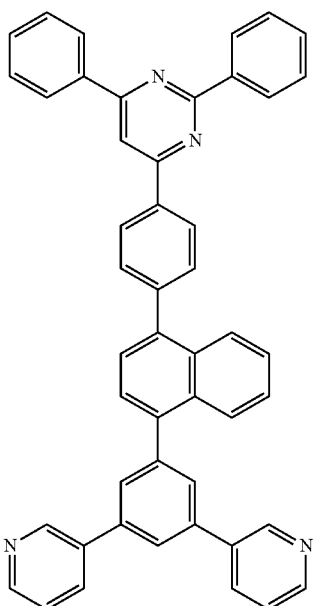
[Compound 4]
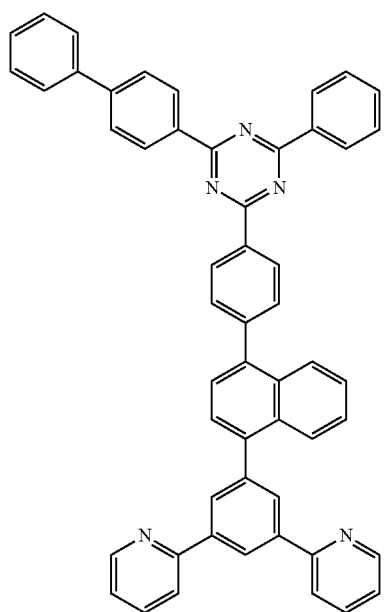
[Compound 6]

[Compound 7]
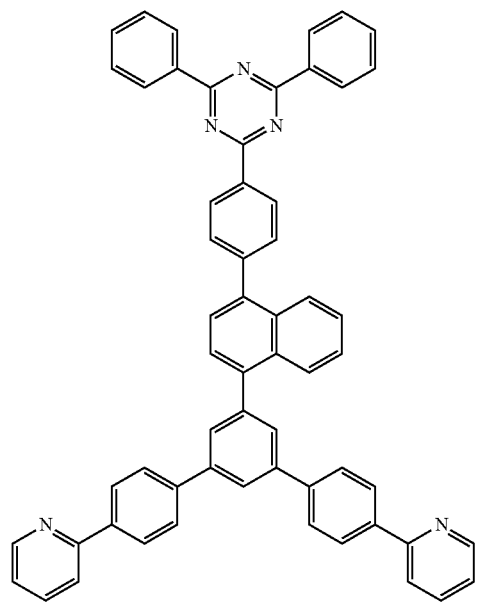
[Compound 9]
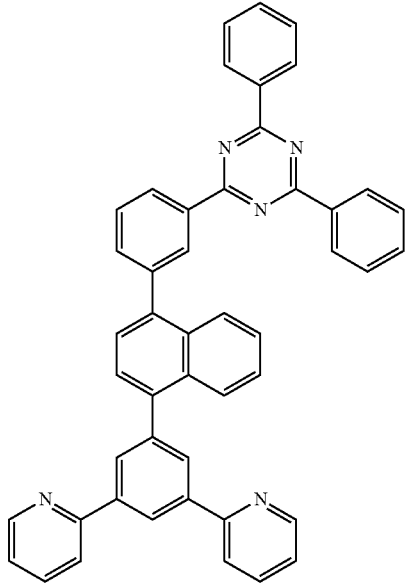
[Compound 8]
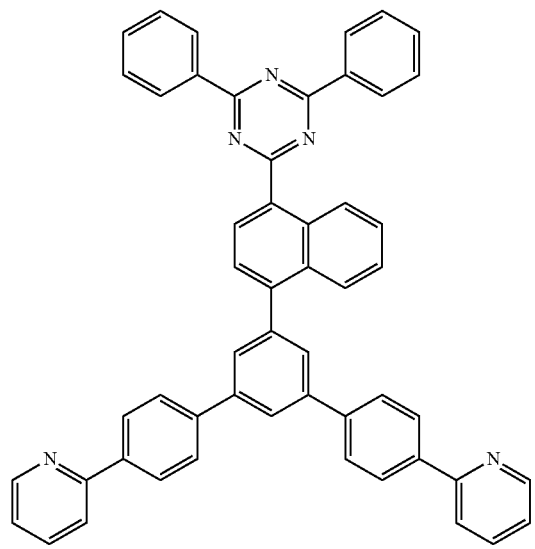
[Compound 10]
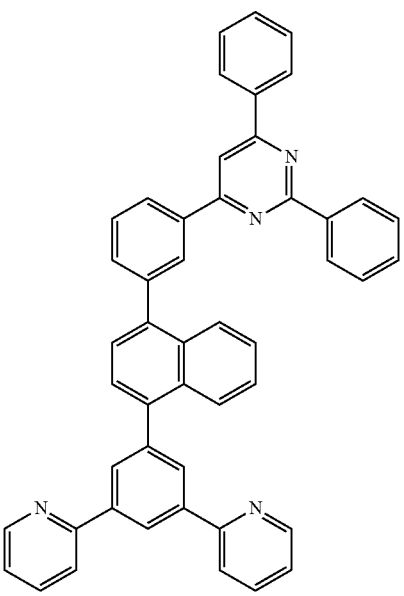

-continued
[Compound 11]
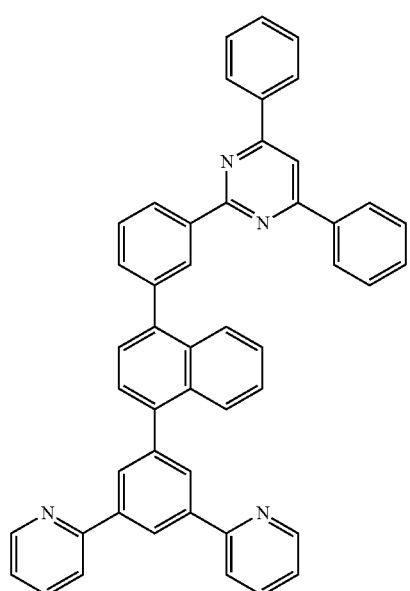
[Compound 12]
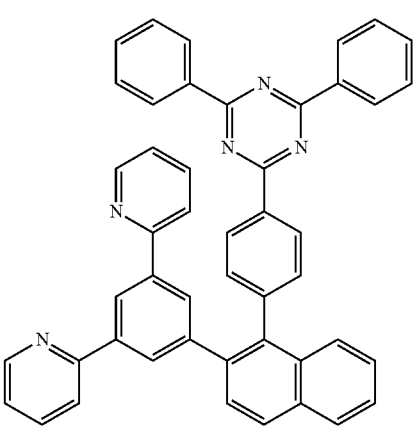
[Compound 13]
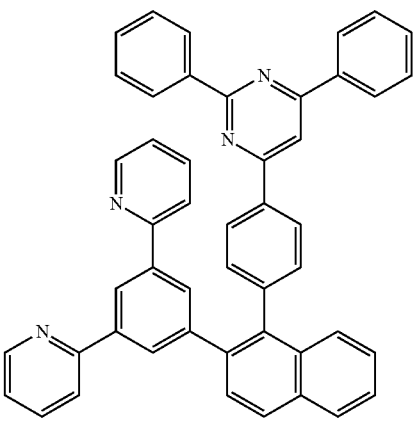
[Compound 14]
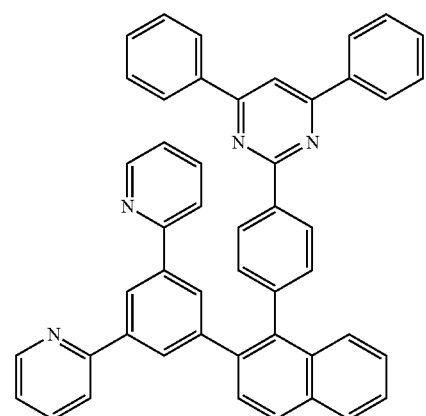
[Compound 15]
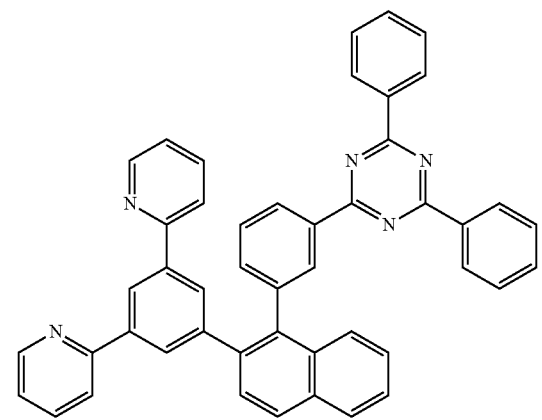
[Compound 16]
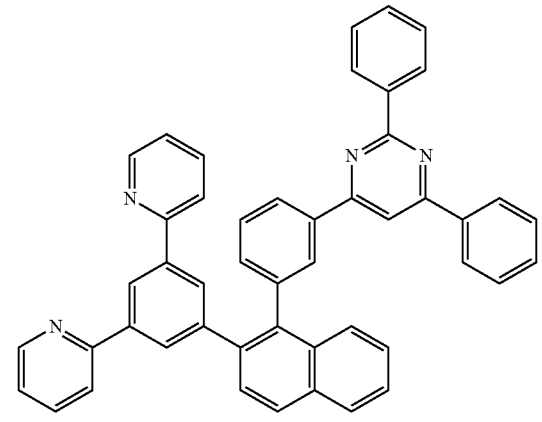

[Compound 17]
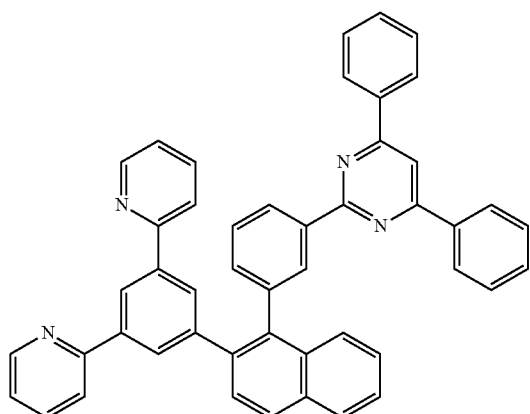
[Compound 19]
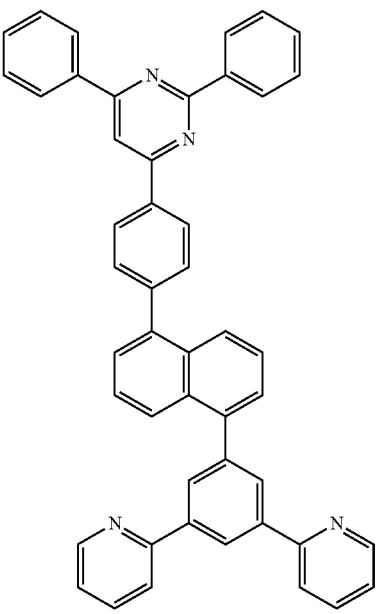
[Compound 18]
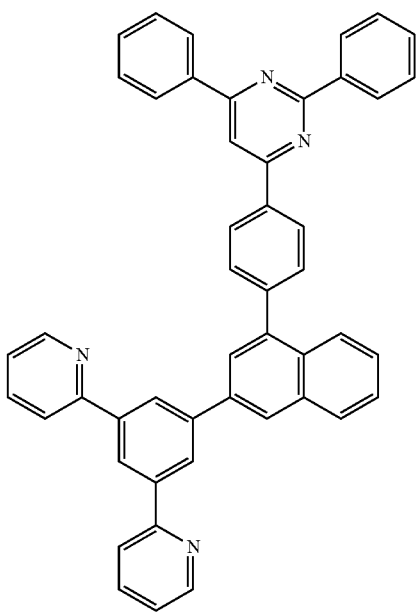
[Compound 20]
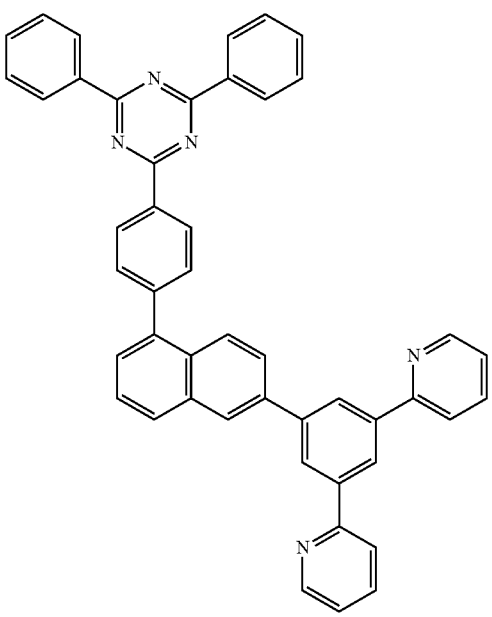

[Compound 21]
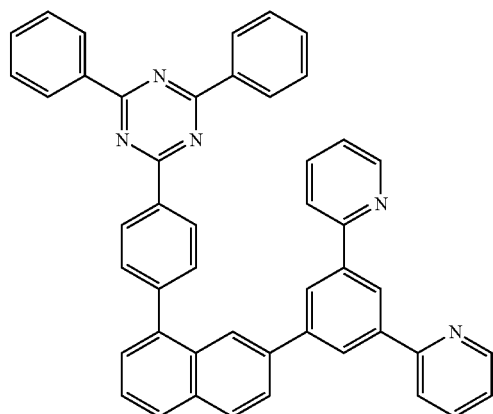
[Compound 24]
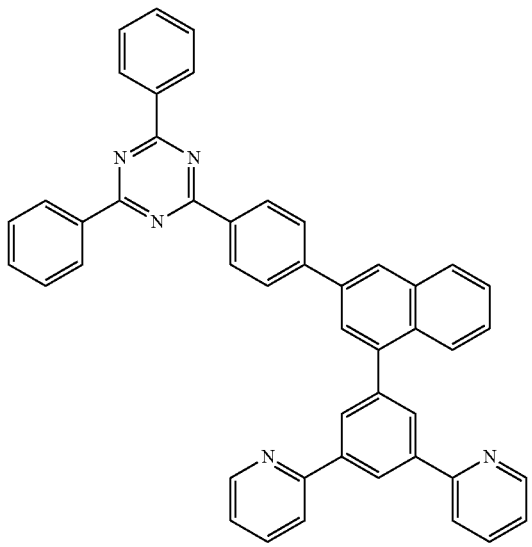
[Compound 22]
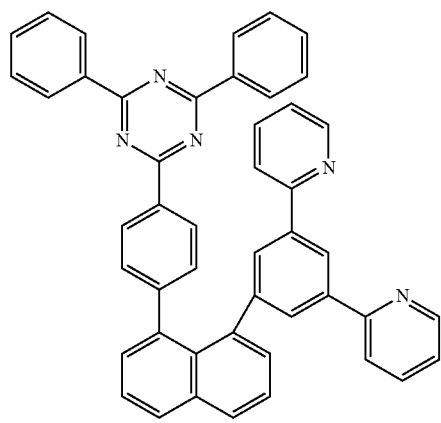
[Compound 23]
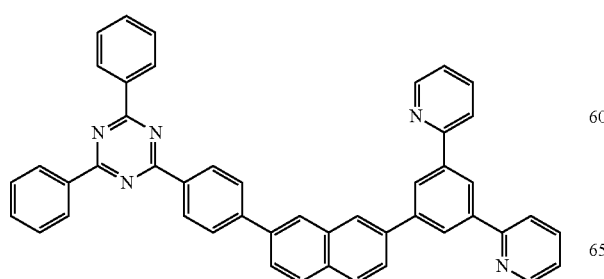
[Compound 25]
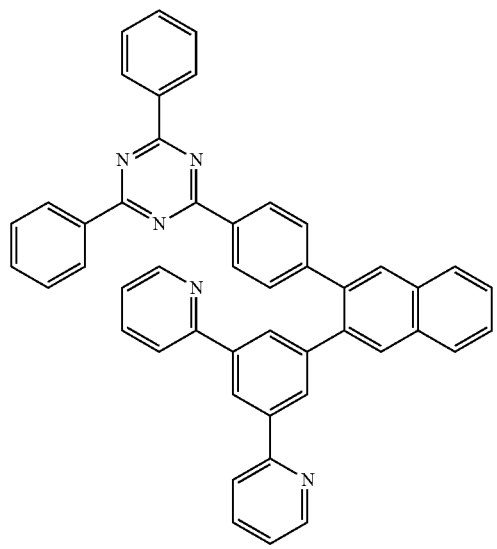

[Compound 26]

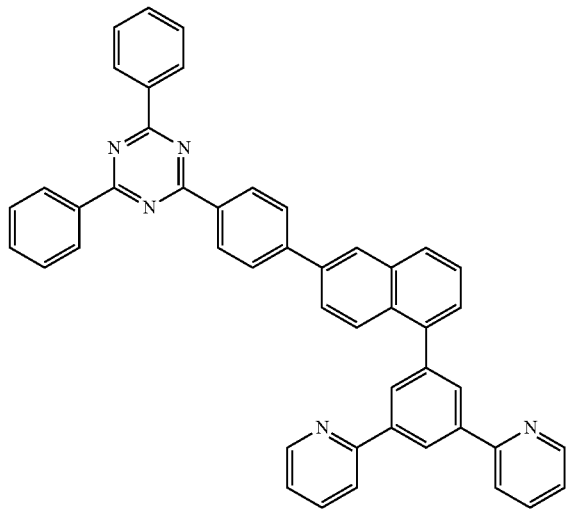

The conjugation length and energy bandgap of the compound are closely related with each other. Specifically, the longer the conjugation length of the compound is, the smaller the bandgap is.

In the present invention, various substituents may be introduced into the core structure to synthesize compounds having various energy bandgaps. A substituent is usually introduced into a core structure having a large energy bandgap to easily adjust the energy bandgap, but when the core structure has a small energy bandgap, it is difficult to significantly adjust the energy bandgap by introducing a substituent.

Further, in the present invention, various substituents may also be introduced into the core structure having the structure as described above to adjust the HOMO and LUMO energy levels of a compound.

In addition, various substituents may be introduced into the core structure having the structure as described above to synthesize a compound having inherent characteristics of the introduced substituent. For example, a substituent usually used for a hole injection layer material, a material for transporting holes, a light emitting layer material, and an electron transport layer material, which are used for manufacturing an organic light emitting device, may be introduced into the core structure to synthesize a material which satisfies conditions required for each organic material layer.

Furthermore, an organic light emitting device according to the present invention is an organic light emitting device including a first electrode, a second electrode, and one or more organic material layers disposed between the first electrode and the second electrode, in which one or more layers of the organic material layers include the compound.

The organic light emitting device of the present invention may be manufactured by typical preparation methods and materials of an organic light emitting device, except that the above-described compound is used to form one or more organic material layers.

The compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

The organic material layer of the organic light emitting device of the present invention may also be composed of a single-layered structure, but may be composed of a multi-layered structure in which two or more organic material layers are stacked. For example, the organic light emitting device of the present invention may have a structure including a hole injection layer, a hole transport layer, a light emitting layer, an electron transport layer, an electron injection layer, and the like as organic material layers. However, the structure of the organic light emitting device is not limited thereto, and may include a fewer number of organic material layers.

Accordingly, in the organic light emitting device of the present invention, the organic material layer may include at least one layer or more of a hole injection layer, a hole transport layer, and a layer which injects and transports holes simultaneously, and at least one layer of the layers may include the compound represented by Chemical Formula 1.

In another exemplary embodiment, the organic material layer includes a light emitting layer, and the light emitting layer includes the compound represented by Chemical Formula 1. As an example, the compound represented by Chemical Formula 1 may be included as a phosphorescent host material of the light emitting layer.

As another example, the organic material layer including the compound represented by Chemical Formula 1 may include the compound represented by Chemical Formula 1 as a host, and may include another organic compound, a metal or a metal compound as a dopant.

As still another example, the organic material layer including the compound represented by Chemical Formula 1 may include the compound represented by Chemical Formula 1 as a host, and may use an iridium (Ir)-based dopant together.

Further, the organic material layer may include at least one layer of an electron transport layer; an electron injection layer; and a layer which transports and injects electrons simultaneously, and one or more layers of the layers may include the compound.

In still another exemplary embodiment, the organic material layer includes an electron transport and hole blocking layer, and the electron transport and hole blocking layer may include the compound.

In the organic material layer having the multi-layered structure, the compound may be included in a light emitting layer; a layer which injects holes/transports holes and emits light simultaneously; a layer which transports holes and emits light simultaneously; or a layer which transports electrons and emits light simultaneously, and the like.

In an exemplary embodiment of the present application, the organic material layer includes a light emitting layer, and the light emitting layer includes a compound of the following Chemical Formula A-1.

[Chemical Formula A-1]

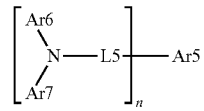

In Chemical Formula A-1, n is an integer of 1 or more,

Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L5 is a direct bond; a substituted or unsubstituted arylene group; or a substituted or unsubstituted heteroarylene group, Ar6 and Ar7 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heterocyclic group, or may combine with each other to form a substituted or unsubstituted ring, and when n is 2 or more, two or more structures in the parenthesis are the same as or different from each other. According to an exemplary embodiment of the present specification, the organic material layer includes a light emitting layer, and the light emitting layer includes the compound represented by Chemical Formula A-1 as a dopant of the light emitting layer.

According to an exemplary embodiment of the present specification, L5 is a direct bond.

According to an exemplary embodiment of the present specification, n is 2.

In an exemplary embodiment of the present specification, Ar5 is a divalent pyrene group which is unsubstituted or substituted with deuterium, a methyl group, an ethyl group, an isopropyl group, or a tert-butyl group; or a divalent chrysene group which is unsubstituted or substituted with deuterium, a methyl group, an ethyl group, or a tert-butyl group.

In an exemplary embodiment of the present specification, Ar5 is a divalent pyrene group which is unsubstituted or substituted with an alkyl group; or a divalent chrysene group which is unsubstituted or substituted with an alkyl group.

In an exemplary embodiment of the present specification, Ar5 is a divalent pyrene group which is unsubstituted or substituted with an alkyl group.

In an exemplary embodiment of the present specification, Ar5 is a divalent pyrene group.

According to an exemplary embodiment of the present specification, Ar6 and Ar7 are the same as or different from each other, and are each independently a substituted or unsubstituted aryl group having 6 to 30 carbon atoms.

According to an exemplary embodiment of the present specification, Ar6 and Ar7 are the same as or different from each other, and are each independently an aryl group which is unsubstituted or substituted with an alkyl group, a nitrile group, or a silyl group substituted with an alkyl group.

According to an exemplary embodiment of the present specification, Ar6 and Ar7 are the same as or different from each other, and are each independently an aryl group which is unsubstituted or substituted with a methyl group, an ethyl group, an isopropyl group, a tert-butyl group, a nitrile group, or a silyl group substituted with an alkyl group.

According to an exemplary embodiment of the present specification, Ar6 and Ar7 are the same as or different from each other, and are each independently an aryl group which is unsubstituted or substituted with silyl group substituted with an alkyl group.

According to an exemplary embodiment of the present specification, Ar6 and Ar7 are the same as or different from each other, and are each independently an aryl group which is unsubstituted or substituted with a trimethylsilyl group.

According to an exemplary embodiment of the present specification, Ar6 and Ar7 are the same as or different from each other, and are each independently a substituted or unsubstituted phenyl group; a substituted or unsubstituted biphenyl group; or a substituted or unsubstituted terphenyl group.

According to an exemplary embodiment of the present specification, Ar6 and Ar7 are the same as or different from each other, and are each independently a phenyl group which is unsubstituted or substituted with a methyl group, an ethyl group, an isopropyl group, a tert-butyl group, a nitrile group, or a trimethylsilyl group.

According to an exemplary embodiment of the present specification, Ar6 and Ar7 are the same as or different from each other, and are each independently a phenyl group which is unsubstituted or substituted with a trimethylsilyl group.

According to an exemplary embodiment of the present specification, Ar6 and Ar7 are the same as or different from each other, and are each independently a substituted or unsubstituted heteroaryl group having 2 to 30 carbon atoms.

According to an exemplary embodiment of the present specification, Ar6 and Ar7 are the same as or different from each other, and are each independently a heteroaryl group which is unsubstituted or substituted with a methyl group, an ethyl group, a tert-butyl group, a nitrile group, a silyl group substituted with an alkyl group, or a phenyl group.

According to an exemplary embodiment of the present specification, Ar6 and Ar7 are the same as or different from each other, and are each independently a dibenzofuran group which is unsubstituted or substituted with a methyl group, an ethyl group, a tert-butyl group, a nitrile group, a trimethylsilyl group, or a phenyl group.

According to an exemplary embodiment of the present specification, Chemical Formula A-1 is selected among the following compounds.

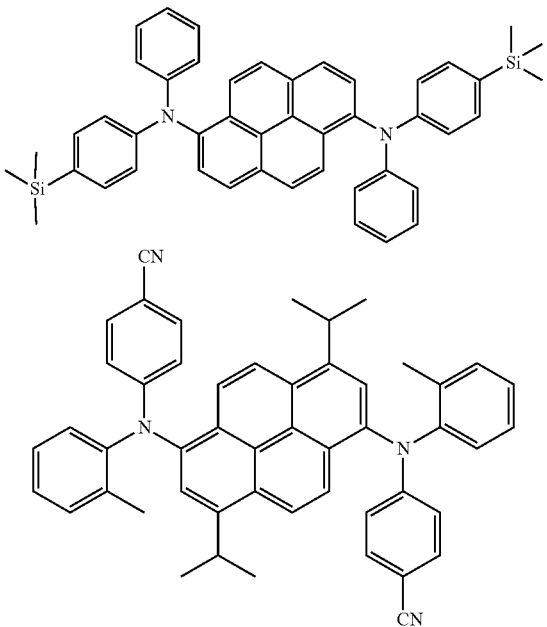

33
-continued
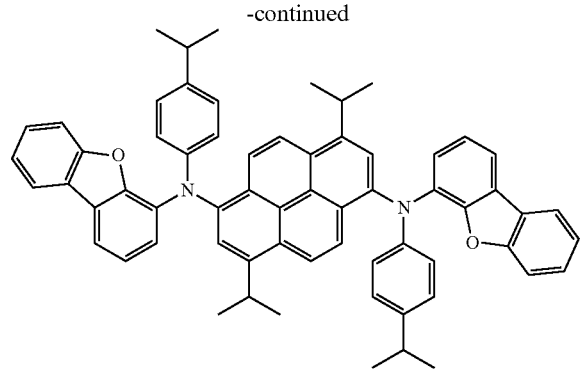
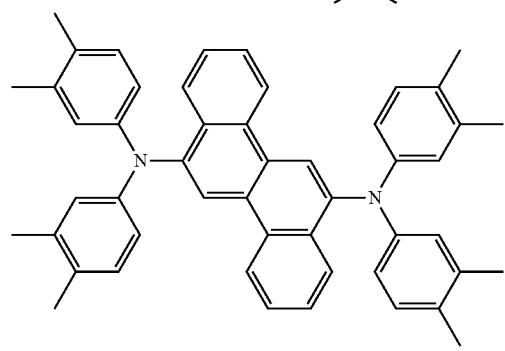
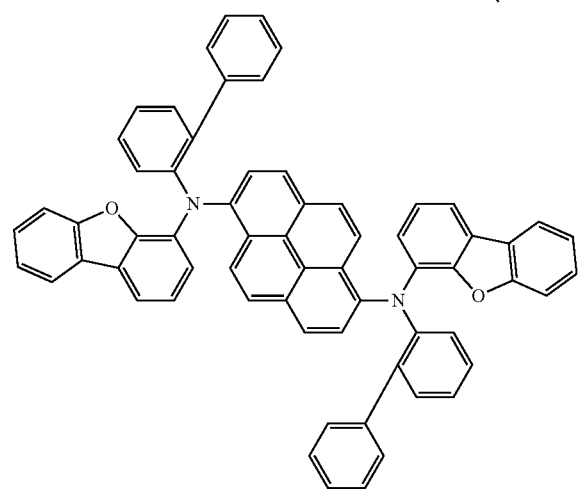
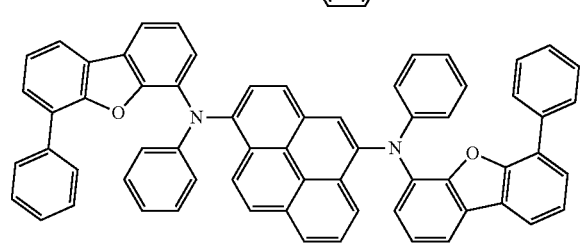
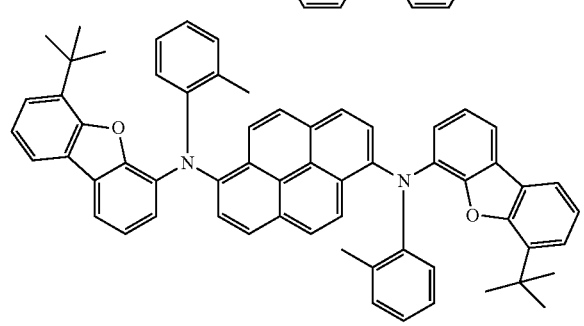
34
-continued
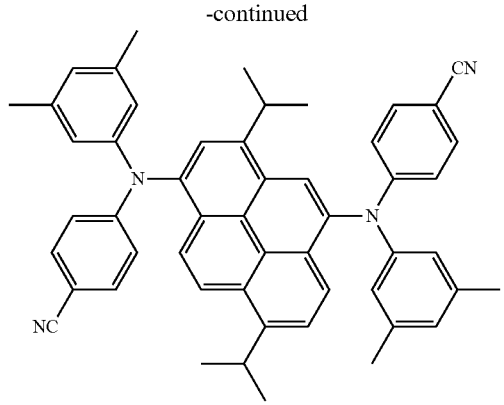

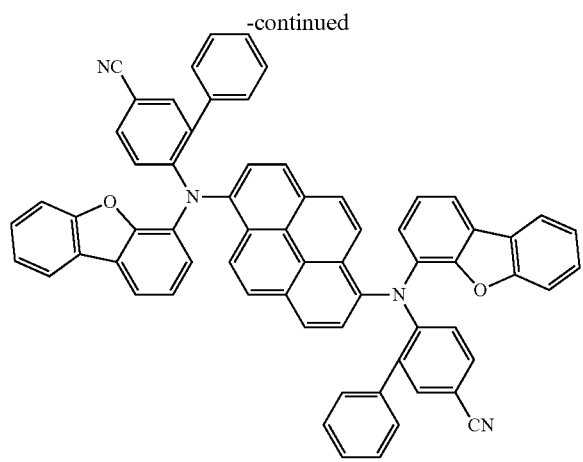

According to an exemplary embodiment of the present specification, the organic material layer includes a light emitting layer, and the light emitting layer includes a compound represented by the following Chemical Formula A-2.

[Chemical Formula A-2]

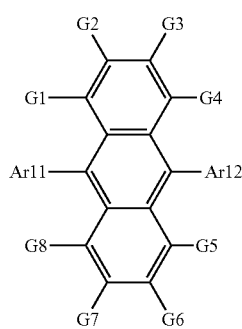

In Chemical Formula A-2,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula A-2 as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted naphthyl group.

According to an exemplary embodiment of the present specification, Ar11 and Ar12 are the same as or different from each other, and are each independently a substituted or unsubstituted 1-naphthyl group.

According to an exemplary embodiment of the present specification, Ar11 and Ar12 are a 1-naphthyl group. According to an exemplary embodiment of the present specification, G1 to G8 are hydrogen.

According to an exemplary embodiment of the present specification, Chemical Formula A-2 is selected from the following compound.

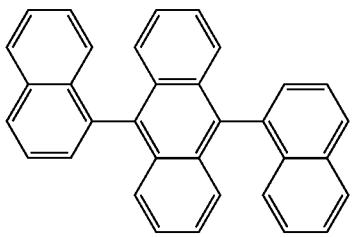 [SMILES: c1ccc2c(-c3c4ccccc4c(-c4cccc5ccccc45)c4ccccc34)cccc2c1]

According to an exemplary embodiment of the present specification, the organic material layer includes a light emitting layer, and the light emitting layer includes the compound represented by Chemical Formula A-1 as a dopant of the light emitting layer, and includes the compound represented by Chemical Formula A-2 as a host of the light emitting layer.

An exemplary embodiment of the present specification provides an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the heterocyclic compound. In one exemplary embodiment, as the two or more organic material layers, two or more may be selected from the group consisting of an electron transport layer, an electron injection layer, a layer which transports and injects electrons simultaneously, and a hole blocking layer.

In an exemplary embodiment of the present specification, the organic material layer includes two or more electron transport layers, and at least one of the two or more electron transport layers includes the heterocyclic compound. Specifically, in an exemplary embodiment of the present specification, the heterocyclic compound may also be included in one layer of the two or more electron transport layers, and may be included in each of the two or more electron transport layers.

In addition, in an exemplary embodiment of the present specification, when the heterocyclic compound is included in each of the two or more electron transport layers, the other materials except for the heterocyclic compound may be the same as or different from each other.

For example, the structure of the organic light emitting device of the present invention may have a structure as illustrated in FIGS. 1 and 2, but is not limited thereto.

FIG. 1 illustrates the structure of an organic light emitting device in which a positive electrode 2, a light emitting layer 3, and a negative electrode 4 are sequentially stacked on a substrate 1. In the structure as described above, the compound may be included in the light emitting layer 3.

FIG. 2 illustrates the structure of an organic light emitting device in which a positive electrode 2, a hole injection layer 5, a hole transport layer 6, a light emitting layer 7, an electron transport layer 8, and a negative electrode 4 are sequentially stacked on a substrate 1. In the structure as described above, the compound may be included in the hole injection layer 5, the hole transport layer 6, the light emitting layer 7, or the electron transport layer 8.

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may also be made by sequentially depositing a negative electrode material, an organic material layer, and a positive electrode material on a substrate.

The organic material layer may have a multi-layered structure including a hole injection layer, a hole transport layer, a light emitting layer, and an electron transport layer, and the like, but is not limited thereto and may be a single-layered structure. Further, the organic material layer may be manufactured with a fewer number of layers by a method such as a solvent process, for example, spin coating, dip coating, doctor blading, a screen printing, inkjet printing, or a thermal transfer method using various polymers, instead of a deposition method.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methyl compound), poly[3,4-(ethylene-1,2-dioxy)compound] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a material which may well receive holes injected from a positive electrode at low voltage, and it is preferred that the highest occupied molecular orbital (HOMO) of the hole injection material is between a work function of a positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polycompound-based electrically conductive polymer, and the like, but are not limited thereto.

The hole transport material is a material which may receive holes transported from a positive electrode or a hole injection layer and transfer the holes to a light emitting layer, and is suitably a material having a large mobility for holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The organic material layer including the compound represented by Chemical Formula 1 may include the compound represented by Chemical Formula 1 as a host, and may use an iridium (Ir)-based dopant together.

The iridium-based complex used as a dopant is as follows.

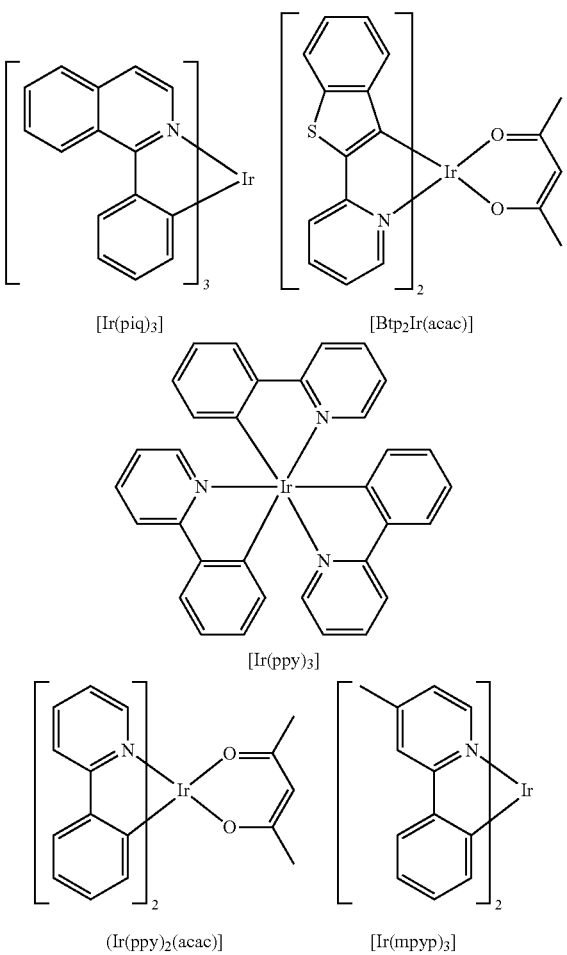

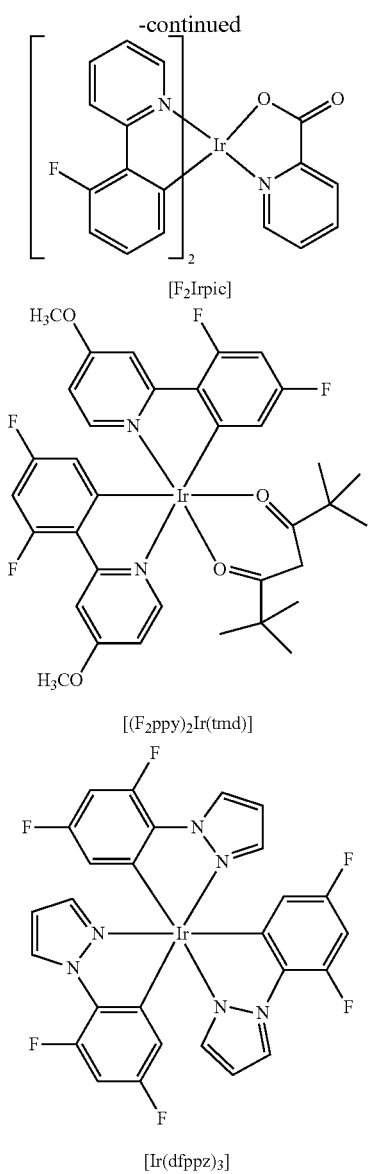

[F₂Irpic]

[(F₂ppy)₂Ir(tmd)]

[Ir(dfppz)₃]

The electron transport material is a material which may well receive electrons injected from a negative electrode and transfer the electrons to a light emitting layer, and is suitably a material having a large mobility for electrons. Specific examples thereof include: an Al complex of 8-hydroxyquinoline; a complex including Alq₃; an organic radical compound; a hydroxyflavone-metal complex, and the like, but are not limited thereto.

The organic light emitting device according to the present invention may be a top emission type, a bottom emission type, or a dual emission type according to the material to be used.

Mode for Invention

The preparation method of the compound of Chemical Formula 1 and the manufacture of an organic light emitting device using the same will be specifically described in the following Examples. However, the following Examples are provided for exemplifying the present invention, and the scope of the present invention is not limited thereby.

PREPARATION EXAMPLES

<Synthesis Example 1>—Preparation of Compound Represented by Compound 1

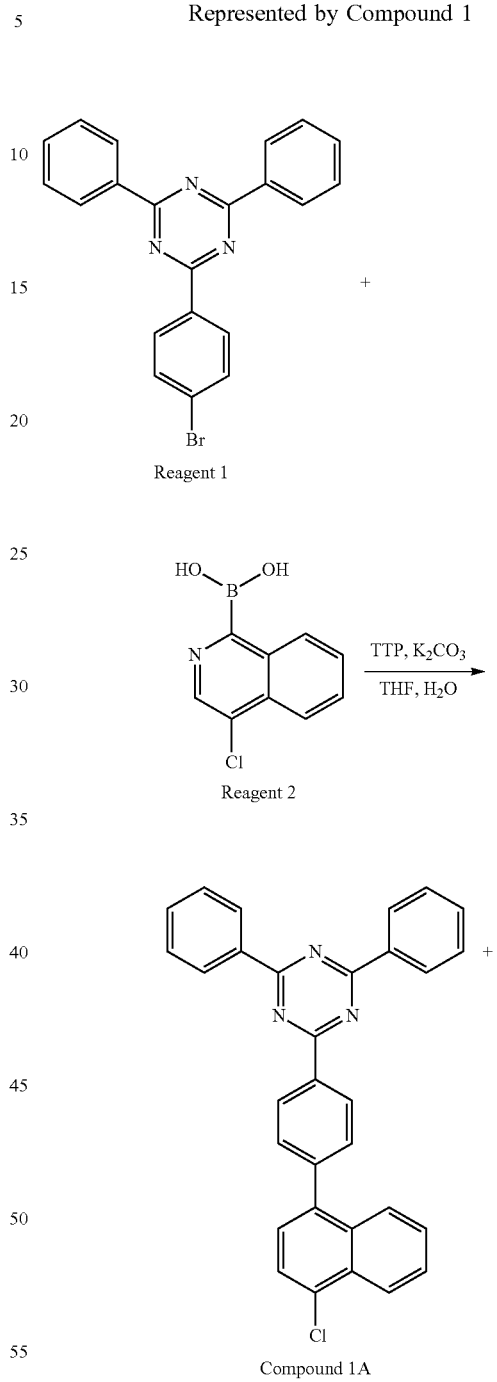

Reagent 1

Reagent 2

Compound 1A

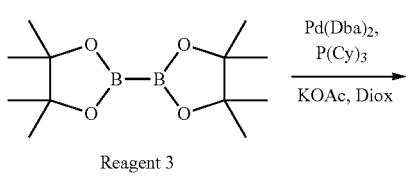

Reagent 3

-continued
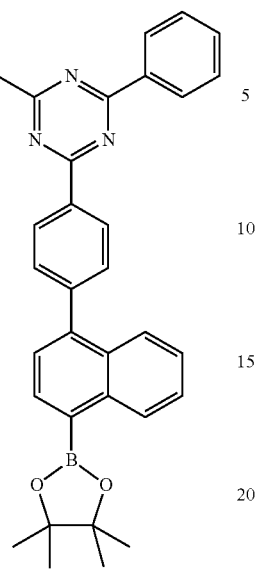
Compound 1B
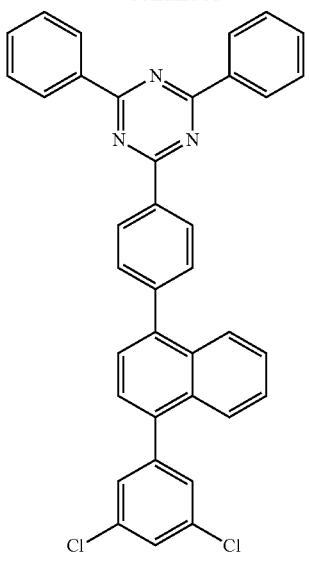
Compound 1C
+
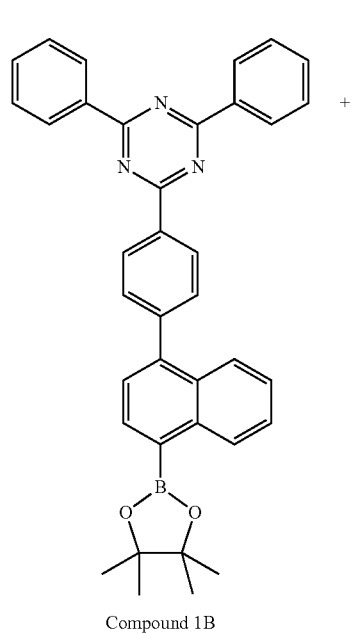
Compound 1B
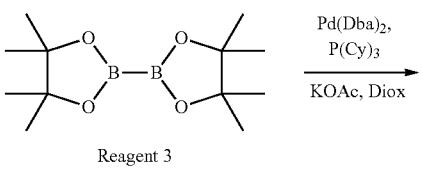
Reagent 3
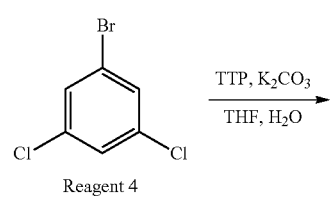
Reagent 4
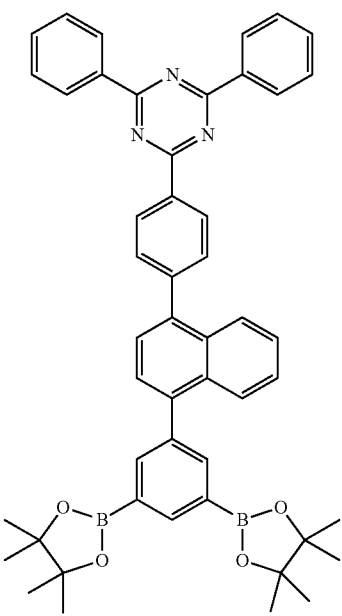
Compound 1D

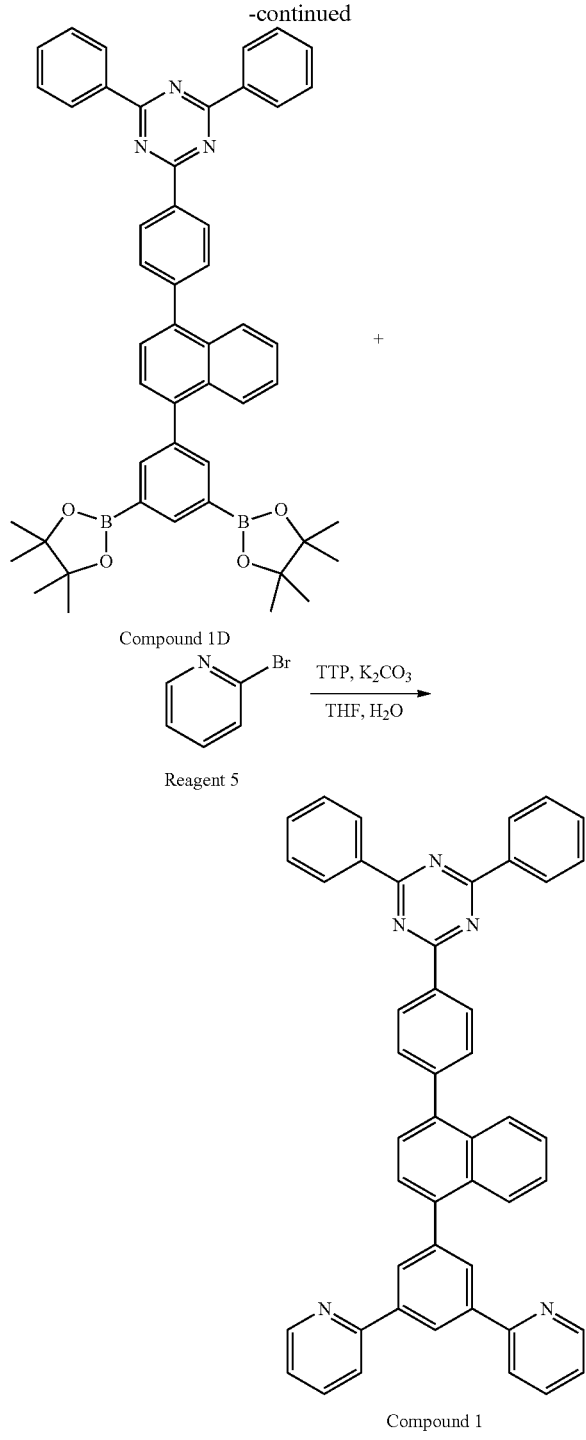

Compound 1D

Reagent 5

Compound 1

(1) Preparation of Compound 1A

Reagent 1 (100.0 g, 257.55 mmol) and Reagent 2 (58.5 g, 206.43 mmol) were put into 1,000 ml of tetrahydrofuran under a nitrogen atmosphere, and the resulting mixture was stirred and refluxed. Thereafter, potassium carbonate (71.2 g, 515.11 mmol) was dissolved in 200 ml of water, the resulting solution was introduced into the mixture, the resulting mixture was sufficiently stirred, and then tetrakis-triphenyl-phosphinopalladium (8.9 g, 7.73 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 1A (112.6 g, 88%). Reagents 1 and 2 were purchased from Aldrich and TCI, respectively.

(2) Preparation of Compound 1B

Compound 1A (70.0 g, 148.95 mmol) was mixed with Reagent 3 (45.4 g, 178.73 mmol) and potassium acetate (43.9 g, 446.845 mmol) under a nitrogen atmosphere, and the resulting mixture was added to 700 ml of dioxane and was heated while being stirred. Bis(dibenzylidineacetone) palladium (2.6 g, 4.47 mmol) and tricyclohexylphosphine (2.5 g, 8.94 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 1B (51 g, 61%).

(3) Preparation of Compound 1C

Compound 1B (31.2 g, 55.57 mmol) and Reagent 4 (12.6 g, 55.57 mmol) were put into 300 ml of tetrahydrofuran under a nitrogen atmosphere, and the resulting mixture was stirred and refluxed. Thereafter, potassium carbonate (23.0 g, 167.70 mmol) was dissolved in 800 ml of water, the resulting solution was introduced into the mixture, the resulting mixture was sufficiently stirred, and then tetrakis-triphenyl-phosphinopalladium (1.9 g, 1.67 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 1C (19.4 g, 60%). Reagent 4 was purchased from Aldrich.

(4) Preparation of Compound 1D

Compound 10 (19.4 g, 34.55 mmol) was mixed with Reagent 3 (18.8 g, 82.92 mmol) and potassium acetate (20.3 g, 207.31 mmol) under a nitrogen atmosphere, and the resulting mixture was added to 300 ml of dioxane and was heated while being stirred. Bis(dibenzylidineacetone)palladium (1.2 g, 2.07 mmol) and tricyclohexylphosphine (1.2 g, 4.15 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 1D (25.4 g, 68%).

(5) Preparation of Compound 1

Compound 1D (20.0 g, 26.19 mmol) and Reagent 5 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 1 (10.6 g, 60%) was prepared through recrystallization. Reagent 5 was purchased from Aldrich.

MS: $[M+H]^+=666$

<Synthesis Example 2>—Preparation of Compound Represented by Compound 2

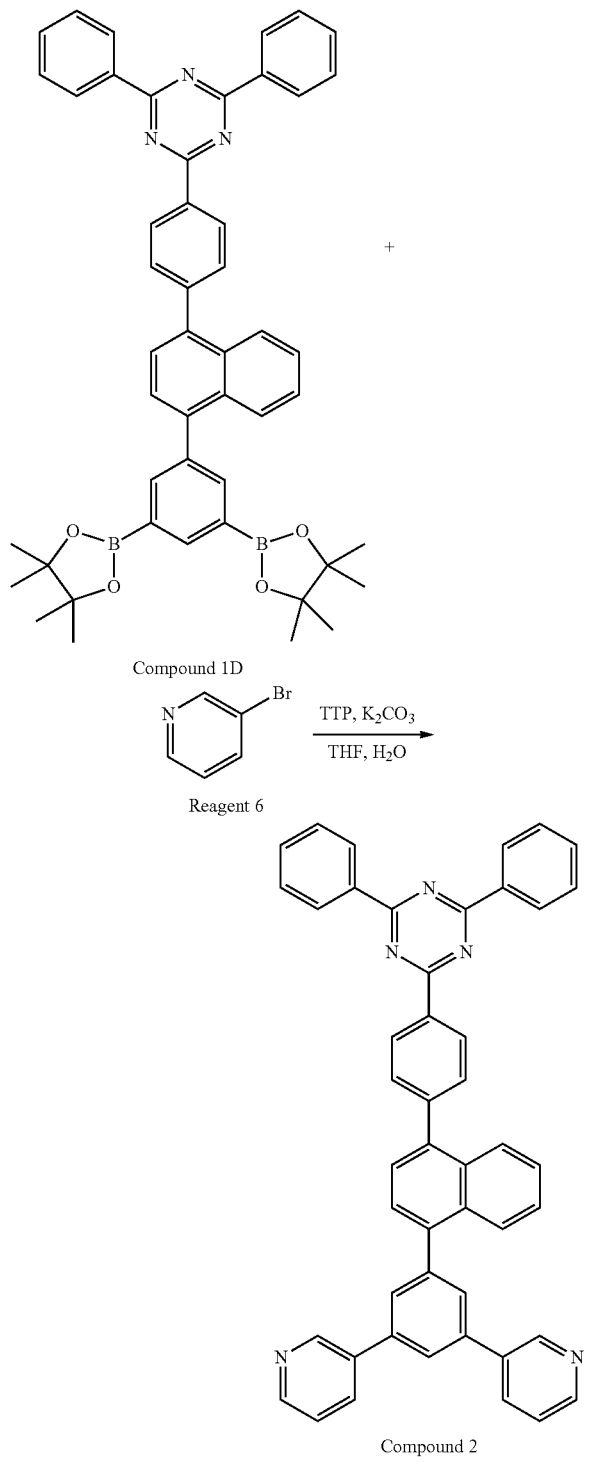

(1) Preparation of Compound 2

Compound 1D (20.0 g, 26.19 mmol) and Reagent 6 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 2 (12.2 g, 71%) was prepared through recrystallization. Reagent 6 was purchased from Aldrich.

MS: $[M+H]^+=666$

<Synthesis Example 3>—Preparation of Compound Represented by Compound 3

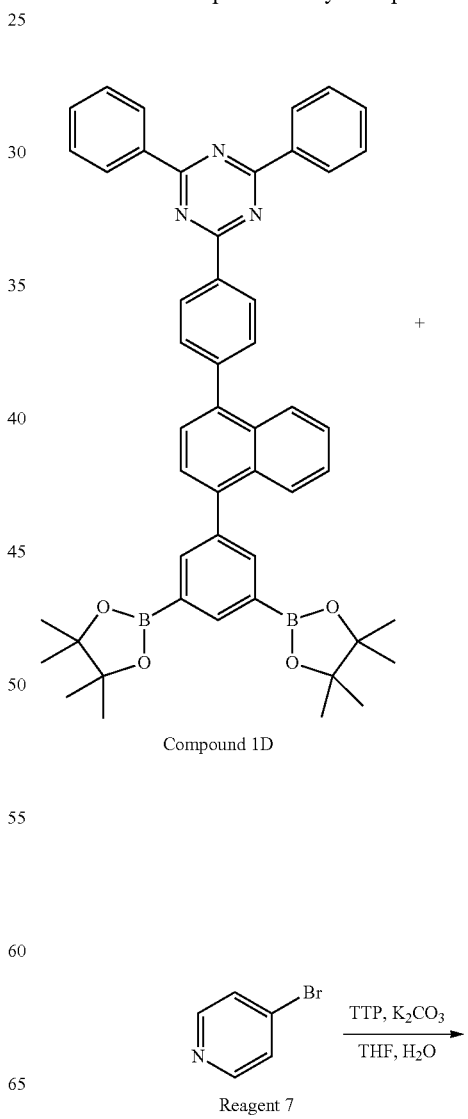

-continued

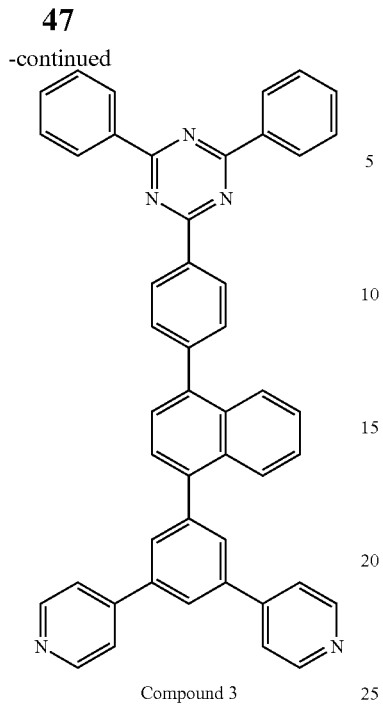

Compound 3

(1) Preparation of Compound 3

Compound 1D (20.0 g, 26.19 mmol) and Reagent 7 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced thereinto, the resulting mixture was sufficiently stirred, and then tetrakistriphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 3 (8.2 g, 42%) was prepared through recrystallization. Reagent 7 was purchased from Aldrich.

MS: [M+H]⁺=666

<Synthesis Example 4>—Preparation of Compound Represented by Compound 4

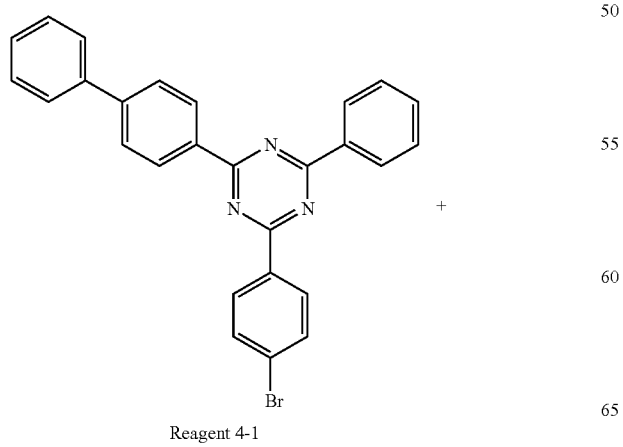

Reagent 4-1

-continued

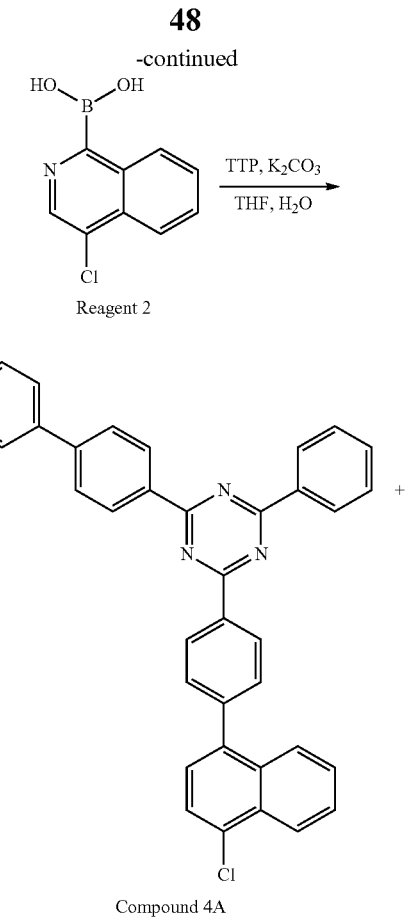

Reagent 2

Compound 4A

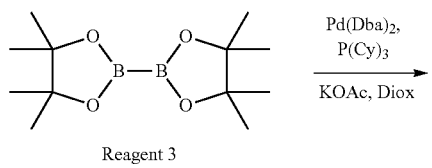

Reagent 3

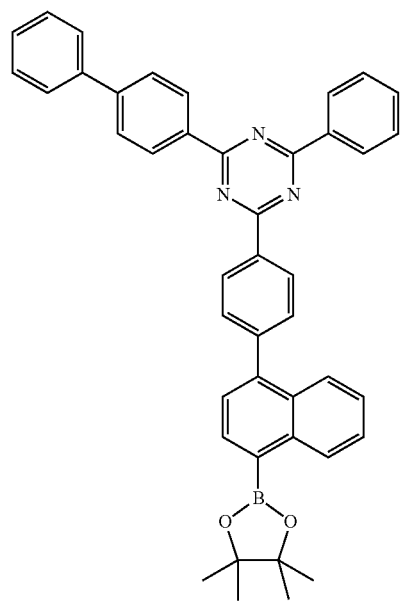

Compound 4B

49
-continued
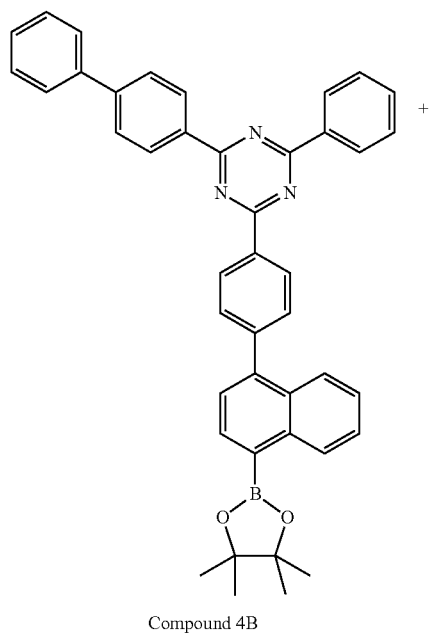
Compound 4B
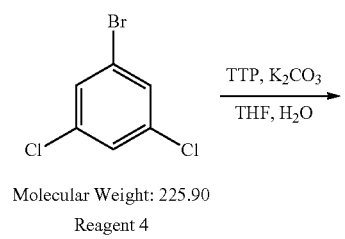
Molecular Weight: 225.90
Reagent 4
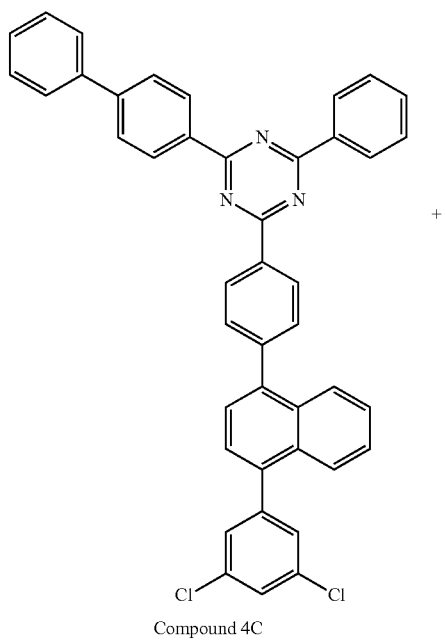
Compound 4C
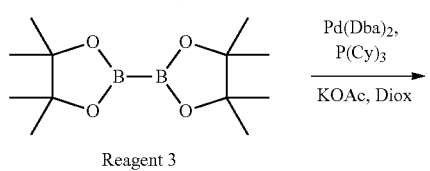
Reagent 3
Pd(Dba)$_2$,
P(Cy)$_3$
KOAc, Diox
TTP, K$_2$CO$_3$
THF, H$_2$O
+
50
-continued
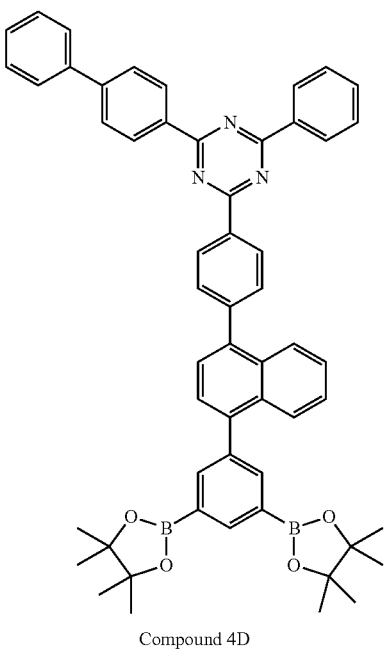
Compound 4D
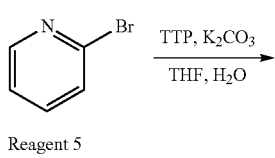
Compound 4D
Reagent 5
TTP, K$_2$CO$_3$
THF, H$_2$O
+

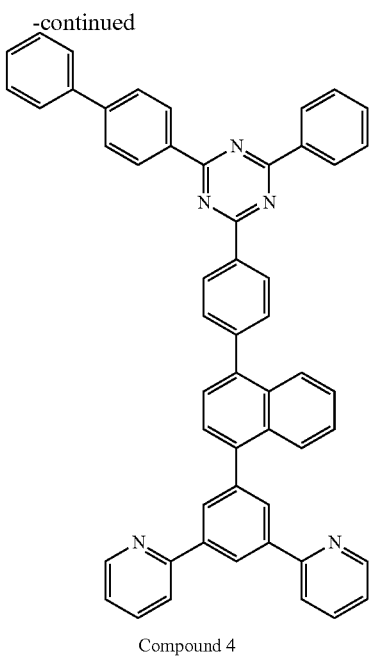

Compound 4

(1) Preparation of Compound 4A

Reagent 4-1 (100.0 g, 215.35 mmol) and Reagent 2 (48.9 g, 236.88 mmol) were put into 1,000 ml of tetrahydrofuran under a nitrogen atmosphere, and the resulting mixture was stirred and refluxed. Thereafter, potassium carbonate (59.5 g, 430.69 mmol) was dissolved in 200 ml of water, the resulting solution was introduced thereinto, the resulting mixture was sufficiently stirred, and then tetrakistriphenyl-phosphinopalladium (7.5 g, 6.46 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 4A (103 g, 85%). Reagents 4-1 and 2 were purchased from Aldrich and TCI, respectively.

(2) Preparation of Compound 4B

Compound 4A (70.0 g, 128.21 mmol) was mixed with Reagent 3 (39.1 g, 153.85 mmol) and potassium acetate (37.7 g, 384.62 mmol) under a nitrogen atmosphere, and the resulting mixture was added to 700 ml of dioxane and was heated while being stirred. Bis(dibenzylidineacetone)palladium (2.2 g, 3.85 mmol) and tricyclohexylphosphine (2.2 g, 3.85 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 4B (62 g, 75%).

(3) Preparation of Compound 4C

Compound 4B (30.0 g, 47.05 mmol) and Reagent 4 (10.6 g, 47.05 mmol) were put into 300 ml of tetrahydrofuran under a nitrogen atmosphere, and the resulting mixture was stirred and refluxed. Thereafter, potassium carbonate (19.5 g, 141.16 mmol) was dissolved in 800 ml of water, the resulting solution was introduced into the mixture, the resulting mixture was sufficiently stirred, and then tetrakistriphenyl-phosphinopalladium (1.6 g, 1.41 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 4C (19.7 g, 64%). Reagent 4 was purchased from Aldrich.

(4) Preparation of Compound 4D

Compound 4C (19.7 g, 34.55 mmol) was mixed with Reagent 3 (16.3 g, 72.01 mmol) and potassium acetate (17.6 g, 180.02 mmol) under a nitrogen atmosphere, and the resulting mixture was added to 300 ml of dioxane and was heated while being stirred. Bis(dibenzylidineacetone)palladium (1.0 g, 1.8 mmol) and tricyclohexylphosphine (1.0 g, 3.6 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 4D (25.4 g, 68%).

(5) Preparation of Compound 4

Compound 4D (20.0 g, 23.8 mmol) and Reagent 5 (4.1 g, 26.19 mmol) were put into 300 ml of tetrahydrofuran under a nitrogen atmosphere, and the resulting mixture was stirred and refluxed. Thereafter, potassium carbonate (9.9 g, 71.46 mmol) was dissolved in 50 ml of water, the resulting solution was introduced into the mixture, the resulting mixture was sufficiently stirred, and then tetrakistriphenyl-phosphinopalladium (0.8 g, 0.71 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 4 (11.8 g, 67%) was prepared through recrystallization. Reagent 5 was purchased from Aldrich.

MS: $[M+H]^+=742$

<Synthesis Example 5>—Preparation of Compound Represented by Compound 7

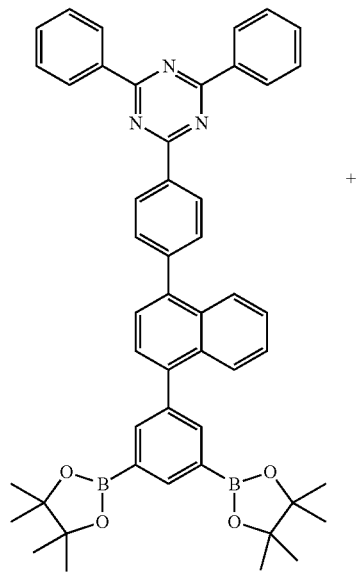

Molecular Weight: 763.55
Compound 1D

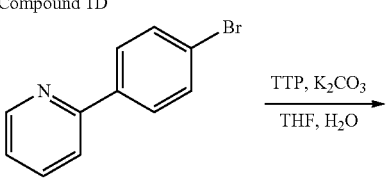

Molecular Weight: 234.10
Reagent 5-1

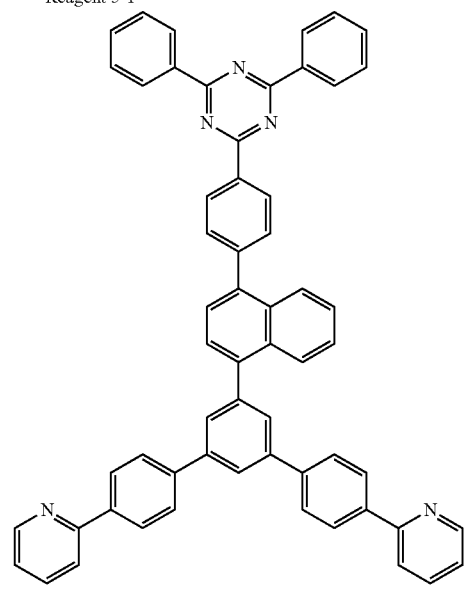

Molecular Weight: 818.00
Compound 7

(1) Preparation of Compound 7

Compound 1D (20.0 g, 26.19 mmol) and Reagent 5-1 (12.3 g, 52.41 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 7 (10.9 g, 51%) was prepared through recrystallization. Reagent 5-1 was purchased from Aldrich.

MS: $[M+H]^+$=819

<Synthesis Example 6>—Preparation of Compound Represented by Compound 8

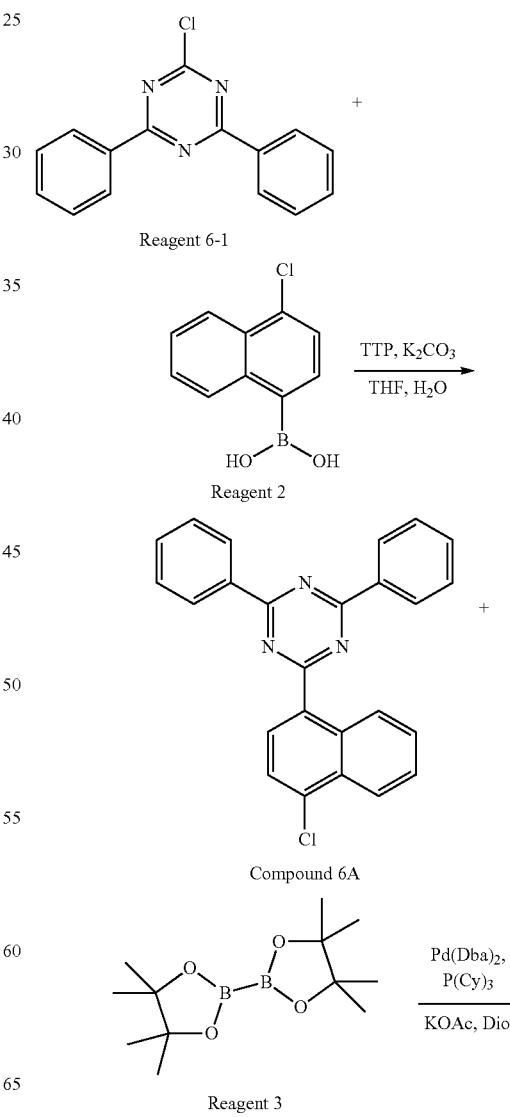

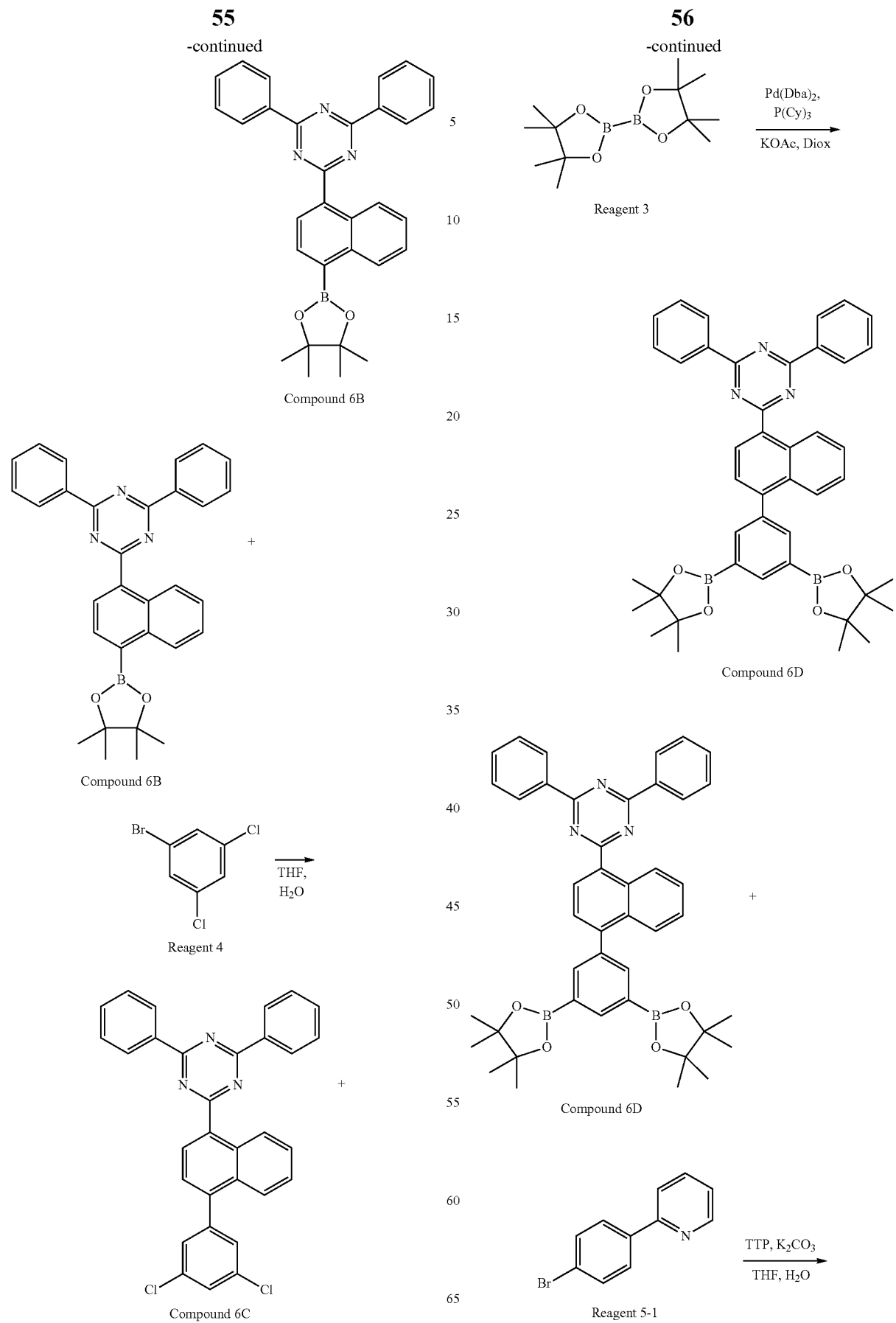

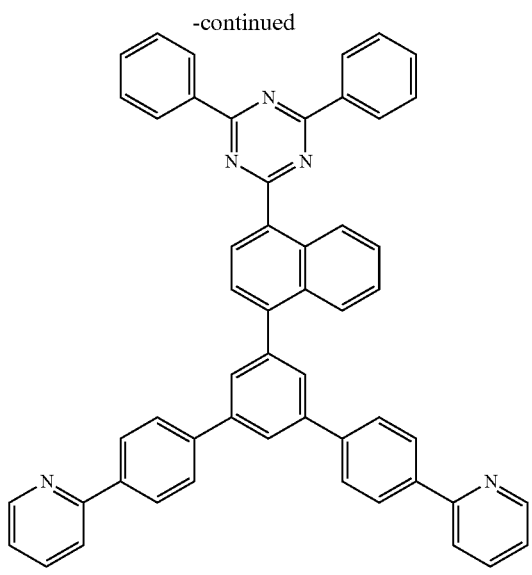

Compound 8

(1) Preparation of Compound 6A

Reagent 6-1 (50.0 g, 187.27 mmol) and Reagent 2 (42.5 g, 205.99 mmol) were put into 1,000 ml of tetrahydrofuran under a nitrogen atmosphere, and the resulting mixture was stirred and refluxed. Thereafter, potassium carbonate (51.8 g, 374.53 mmol) was dissolved in 200 ml of water, the resulting solution was introduced into the mixture, the resulting mixture was sufficiently stirred, and then tetrakis-triphenyl-phosphinopalladium (6.5 g, 5.62 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 6A (52.3 g, 71%). Reagents 6-1 and 2 were purchased from Aldrich and TCI, respectively.

(2) Preparation of Compound 6B

Compound 6A (52.3 g, 133.08 mmol) was mixed with Reagent 3 (40.6 g, 159.69 mmol) and potassium acetate (39.2 g, 399.24 mmol) under a nitrogen atmosphere, and the resulting mixture was added to 400 ml of dioxane and was heated while being stirred. Bis(dibenzylidineacetone)palladium (2.3 g, 3.99 mmol) and tricyclohexylphosphine (2.2 g, 7.98 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 6B (42 g, 66%).

(3) Preparation of Compound 6C

Compound 6B (42.0 g, 86.60 mmol) and Reagent 4 (19.6 g, 86.60 mmol) were put into 500 ml of tetrahydrofuran under a nitrogen atmosphere, and the resulting mixture was stirred and refluxed. Thereafter, potassium carbonate (35.9 g, 259.79 mmol) was dissolved in 200 ml of water, the resulting solution was introduced into the mixture, the resulting mixture was sufficiently stirred, and then tetrakis-triphenyl-phosphinopalladium (3.0 g, 2.6 mmol) was introduced thereinto. After the reaction for 12 hours, the temperature of the product was lowered to normal temperature and a produced solid was filtered. After the filtration, the solid was washed with 200 ml of tetrahydrofuran, 500 ml of ethyl acetate, 500 ml of water, and 300 ml of ethanol. The resulting product was dried to prepare Compound 6C (33.5 g, 77%). Reagent 4 was purchased from Aldrich.

(4) Preparation of Compound 6D

Compound 6C (33.5 g, 66.6 mmol) was mixed with Reagent 3 (36.1 g, 159.84 mmol) and potassium acetate (39.2 g, 399.60 mmol) under a nitrogen atmosphere, and the resulting mixture was added to 300 ml of dioxane and was heated while being stirred. Bis(dibenzylidineacetone)palladium (2.3 g, 4.0 mmol) and tricyclohexylphosphine (2.2 g, 7.99 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 6D (38.9 g, 85%).

(5) Preparation of Compound 8

Compound 6D (20.0 g, 29.11 mmol) and Reagent 5-1 (13.6 g, 58.22 mmol) were put into 300 ml of tetrahydrofuran under a nitrogen atmosphere, and the resulting mixture was stirred and refluxed. Thereafter, potassium carbonate (12.1 g, 87.34 mmol) was dissolved in 50 ml of water, the resulting solution was introduced into the mixture, the resulting mixture was sufficiently stirred, and then tetrakis-triphenyl-phosphinopalladium (1.0 g, 0.87 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 8 (8.8 g, 41%) was prepared through recrystallization. Reagent 5-1 was purchased from Aldrich.

MS: $[M+H]^+=741$

<Synthesis Example 7>—Preparation of Compound Represented by Compound 9

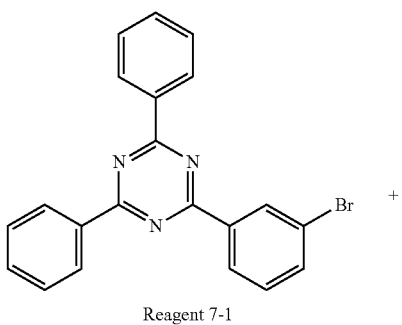

Reagent 7-1

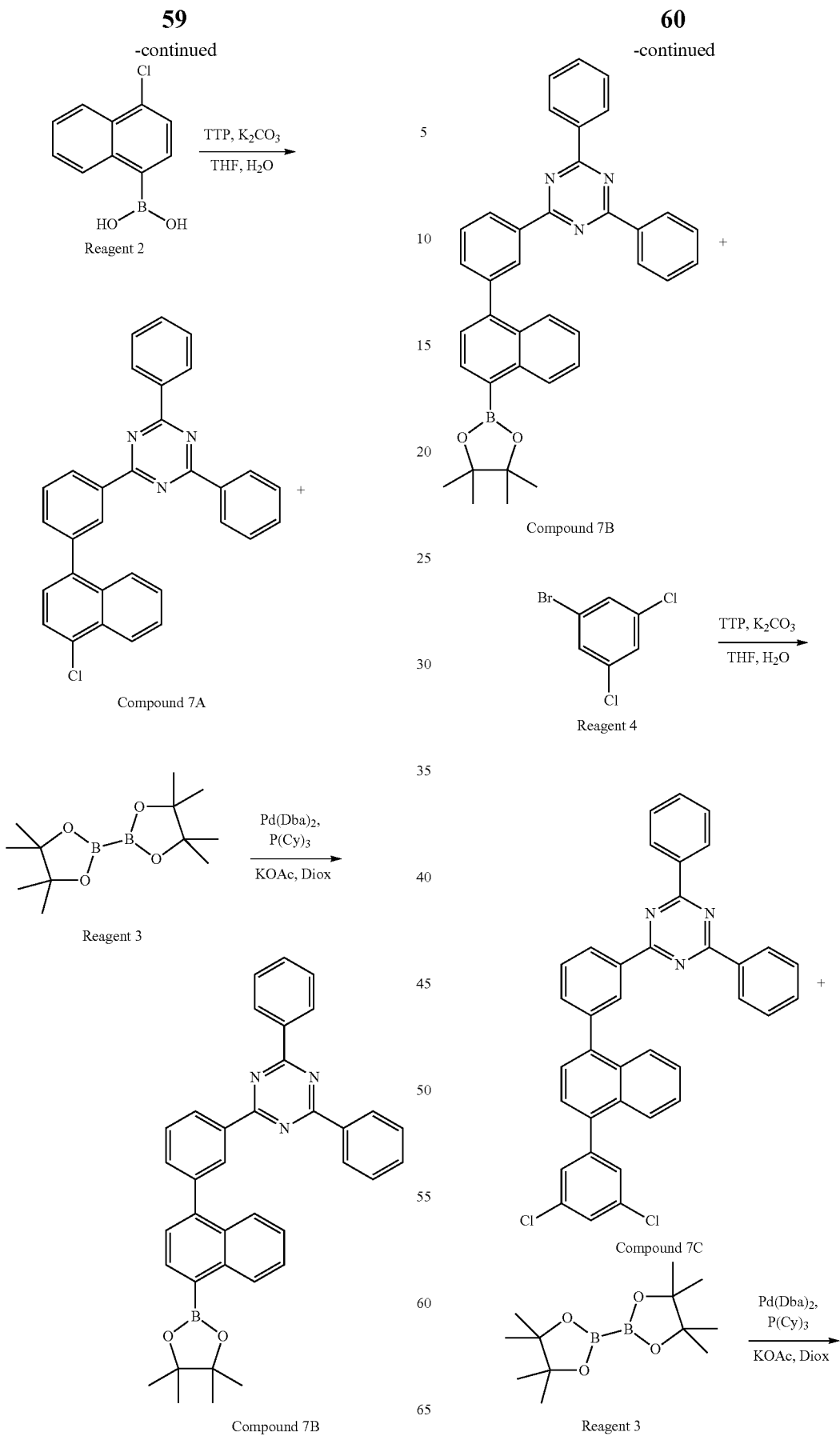

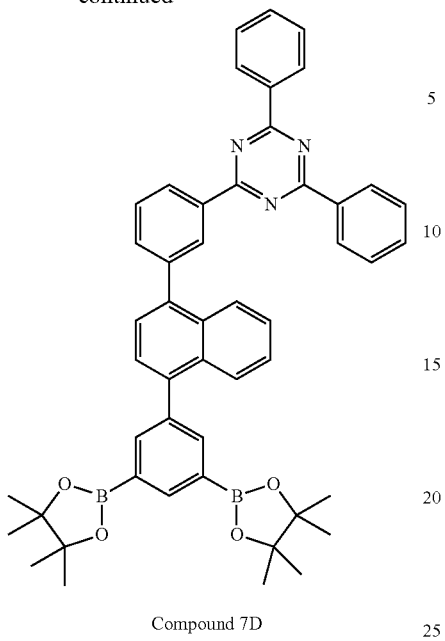

Compound 7D

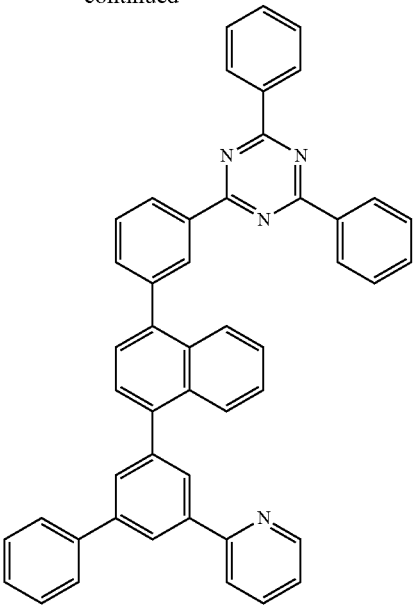

Compound 9

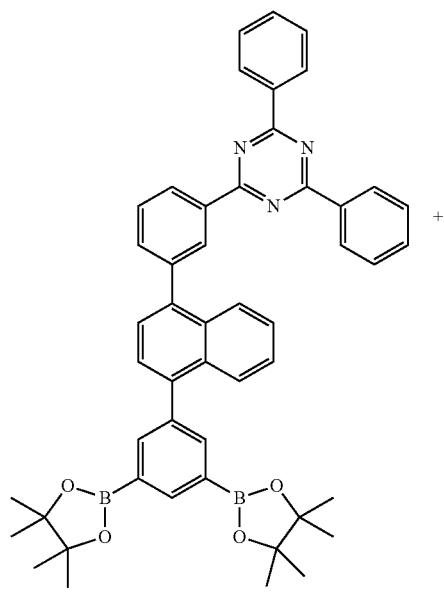

Compound 7D

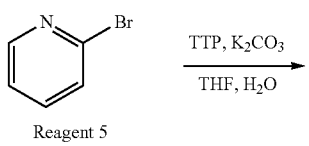

Reagent 5

$\xrightarrow{\text{TTP, K}_2\text{CO}_3}{\text{THF, H}_2\text{O}}$ (1) Preparation of Compound 7A Reagent 7-1 (100.0 g, 257.55 mmol) and Reagent 2 (58.5 g, 206.43 mmol) were put into 1,000 ml of tetrahydrofuran under a nitrogen atmosphere, and the resulting mixture was stirred and refluxed. Thereafter, potassium carbonate (71.2 g, 515.11 mmol) was dissolved in 200 ml of water, the resulting solution was introduced into the mixture, the resulting mixture was sufficiently stirred, and then tetrakis-triphenyl-phosphinopalladium (8.9 g, 7.73 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 7A (98.6 g, 77%). Reagents 7-1 and 2 were purchased from Aldrich and TCI, respectively.

(2) Preparation of Compound 7B

Compound 7A (70.0 g, 148.95 mmol) was mixed with Reagent 3 (45.4 g, 178.73 mmol) and potassium acetate (43.9 g, 446.845 mmol) under a nitrogen atmosphere, and the resulting mixture was added to 700 ml of dioxane and was heated while being stirred. Bis(dibenzylidineacetone)palladium (2.6 g, 4.47 mmol) and tricyclohexylphosphine (2.5 g, 8.94 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 7B (58 g, 70%).

(3) Preparation of Compound 7C

Compound 7B (31.2 g, 55.57 mmol) and Reagent 4 (12.6 g, 55.57 mmol) were put into 300 ml of tetrahydrofuran under a nitrogen atmosphere, and the resulting mixture was stirred and refluxed. Thereafter, potassium carbonate (23.0 g, 167.70 mmol) was dissolved in 800 ml of water, the resulting solution was introduced into the mixture, the resulting mixture was sufficiently stirred, and then tetrakis-triphenyl-phosphinopalladium (1.9 g, 1.67 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 7C (26 g, 80%). Reagent 4 was purchased from Aldrich.

(4) Preparation of Compound 7D

Compound 7C (19.4 g, 34.55 mmol) was mixed with Reagent 3 (18.8 g, 82.92 mmol) and potassium acetate (20.3 g, 207.31 mmol) under a nitrogen atmosphere, and the resulting mixture was added to 300 ml of dioxane and was heated while being stirred. Bis(dibenzylidineacetone)palladium (1.2 g, 2.07 mmol) and tricyclohexylphosphine (1.2 g, 4.15 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 7D (28 g, 75%).

(5) Preparation of Compound 9

Compound 7D (20.0 g, 26.19 mmol) and Reagent 5 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound 9 (12.6 g, 70%) was prepared through recrystallization. Reagent 5 was purchased from Aldrich.

MS: [M+H]⁺=666

<Synthesis Example 8>—Preparation of Compound Represented by Compound 12

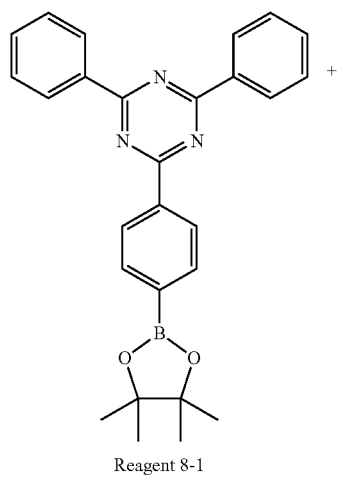

Reagent 8-1

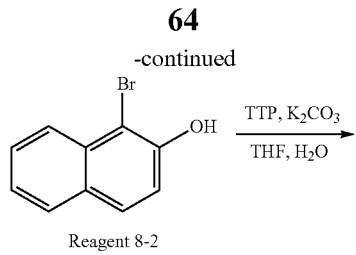

Reagent 8-2

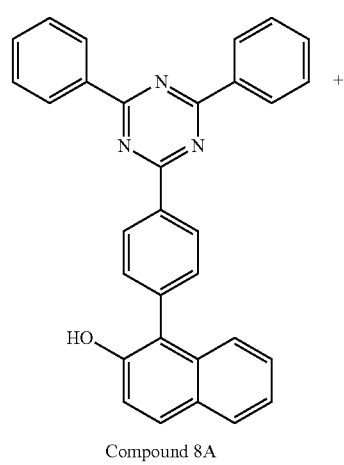

Compound 8A

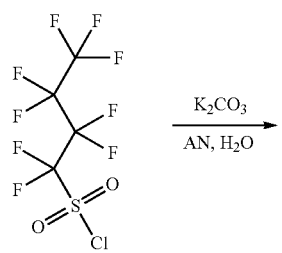

Reagent B-3

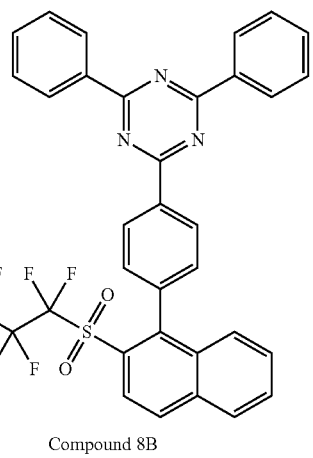

Compound 8B

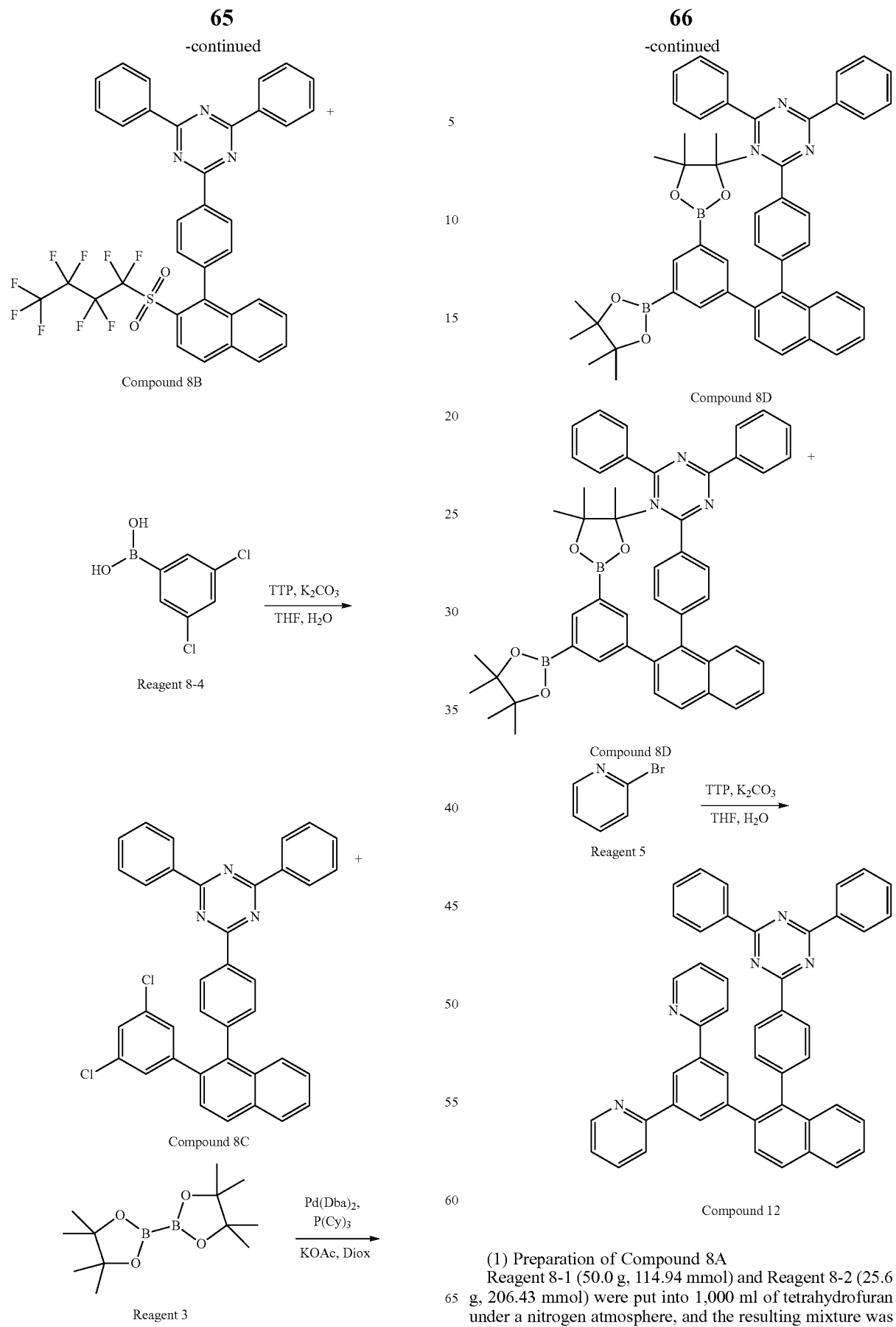
(1) Preparation of Compound 8A
Reagent 8-1 (50.0 g, 114.94 mmol) and Reagent 8-2 (25.6 g, 206.43 mmol) were put into 1,000 ml of tetrahydrofuran under a nitrogen atmosphere, and the resulting mixture was stirred and refluxed. Thereafter, potassium carbonate (71.2 g, 515.11 mmol) was dissolved in 200 ml of water, the resulting solution was introduced into the mixture, the resulting mixture was sufficiently stirred, and then tetrakis-triphenyl-phosphinopalladium (8.9 g, 7.73 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 8A (42 g, 81%). Reagents 8-1 and 8-2 were purchased from Aldrich and TCI, respectively.

(2) Preparation of Compound 8B

Compound 8A (42.0 g, 93.02 mmol) was dissolved in 500 ml of acetonitrile under a nitrogen atmosphere, and then potassium carbonate (25.7 g, 186.03 mmol) was dissolved in 100 ml of water, the resulting solution was introduced thereinto, Reagent 8-3 (42.1 g, 139.53 mmol) was slowly introduced thereinto, and the resulting mixture was heated at 70° C. and stirred for 1 hour. After the reaction was terminated, the temperature of the product was lowered to normal temperature, and then the mixture was filtered. Water was poured into the filtrate, and the mixture was washed with ethanol, and then dried to prepare Compound 8B (62 g, 90%).

(3) Preparation of Compound 8C

Compound 8B (62 g, 86.47 mmol) and Reagent 8-4 (19.5 g, 86.47 mmol) were put into 600 ml of tetrahydrofuran under a nitrogen atmosphere, and the resulting mixture was stirred and refluxed. Thereafter, potassium carbonate (23.0 g, 167.70 mmol) was dissolved in 800 ml of water, the resulting solution was introduced into the mixture, the resulting mixture was sufficiently stirred, and then tetrakis-triphenyl-phosphinopalladium (3.0 g, 2.59 mmol) was introduced thereinto. After the reaction for 12 hours, the temperature of the product was lowered to normal temperature and a produced solid was filtered. After the filtration, the solid was washed with 200 ml of tetrahydrofuran, 500 ml of ethyl acetate, 500 ml of water, and 300 ml of ethanol. The resulting product was dried to prepare Compound 8C (30.6 g, 61%).

(4) Preparation of Compound 8D

Compound 8C (30.6 g, 52.71 mmol) was mixed with Reagent 3 (15.6 g, 126.51 mmol) and potassium acetate (31 g, 316.27 mmol) under a nitrogen atmosphere, and the resulting mixture was added to 300 ml of dioxane and was heated while being stirred. Bis(dibenzylidineacetone)palladium (0.9 g, 1.58 mmol) and tricyclohexylphosphine (0.9 g, 3.16 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 8D (30.5 g, 87%).

(5) Preparation of Compound 12

Compound 8D (20.0 g, 26.19 mmol) and Reagent 5 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound (12.3 g, 70%) was prepared through recrystallization.

MS: [M+H]$^+$=666

<Synthesis Example 9>—Preparation of Compound Represented by Compound 23

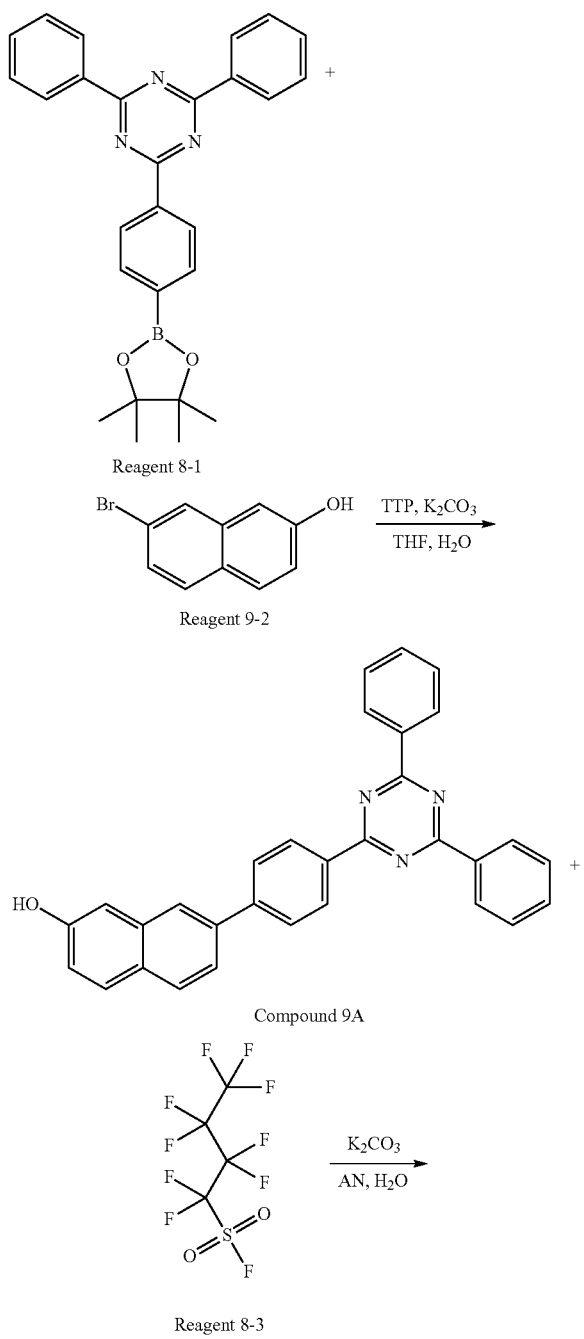

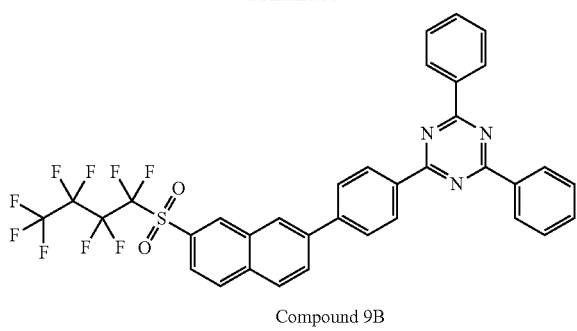

Compound 9B

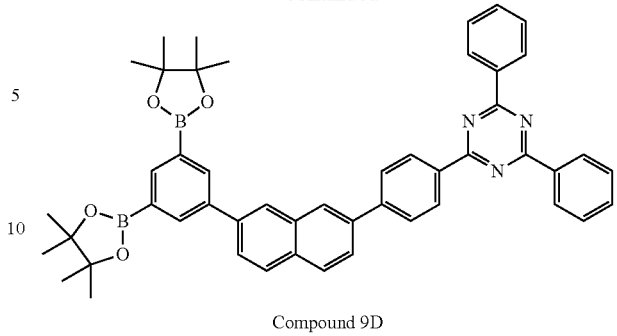

Compound 9D

Compound 9B

Reagent 8-4

Compound 9D

Reagent 5

Compound 23

Compound 9C

Reagent 3

(1) Preparation of Compound 9A

Reagent 8-1 (50.0 g, 114.94 mmol) and Reagent 9-2 (25.6 g, 206.43 mmol) were put into 1,000 ml of tetrahydrofuran under a nitrogen atmosphere, and the resulting mixture was stirred and refluxed. Thereafter, potassium carbonate (71.2 g, 515.11 mmol) was dissolved in 200 ml of water, the resulting solution was introduced into the mixture, the resulting mixture was sufficiently stirred, and then tetrakis-triphenyl-phosphinopalladium (8.9 g, 7.73 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. The resulting product was dried to prepare Compound 9A (42 g, 81%). Reagents 8-1 and 9-2 were purchased from Aldrich and TCI, respectively.

(2) Preparation of Compound 9B

Compound 9A (42.0 g, 93.02 mmol) was dissolved in 500 ml of acetonitrile under a nitrogen atmosphere, and then potassium carbonate (25.7 g, 186.03 mmol) was dissolved in 100 ml of water, the resulting solution was introduced thereinto, Reagent 8-3 (42.1 g, 139.53 mmol) was slowly introduced thereinto, the resulting mixture was heated at 70° C. and stirred for 1 hour. After the reaction was terminated, the temperature of the product was lowered to normal temperature, and then the mixture was filtered. Water was poured into the filtrate, the mixture was washed with ethanol, and then dried to prepare Compound 9B (65 g, 92%).

(3) Preparation of Compound 9C

Compound 9B (62 g, 86.47 mmol) and Reagent 8-4 (19.5 g, 86.47 mmol) were put into 600 ml of tetrahydrofuran under a nitrogen atmosphere, and the resulting mixture was stirred and refluxed. Thereafter, potassium carbonate (23.0 g, 167.70 mmol) was dissolved in 800 ml of water, the resulting solution was introduced into the mixture, the resulting mixture was sufficiently stirred, and then tetrakis-triphenyl-phosphinopalladium (3.0 g, 2.59 mmol) was introduced thereinto. After the reaction for 12 hours, the temperature of the product was lowered to normal temperature and a produced solid was filtered. After the filtration, the solid was washed with 200 ml of tetrahydrofuran, 500 ml of ethyl acetate, 500 ml of water, and 300 ml of ethanol. The resulting product was dried to prepare Compound 9C (33 g, 64%).

(4) Preparation of Compound 9D

Compound 9C (30.6 g, 52.71 mmol) was mixed with Reagent 3 (15.6 g, 126.51 mmol) and potassium acetate (31 g, 316.27 mmol) under a nitrogen atmosphere, and the resulting mixture was added to 300 ml of dioxane and was heated while being stirred. Bis(dibenzylidineacetone)palladium (0.9 g, 1.58 mmol) and tricyclohexylphosphine (0.9 g, 3.16 mmol) were put into the mixture under reflux, and the resulting mixture was heated and stirred for 24 hours. After the reaction was terminated, the temperature of the product was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 9D (33 g, 89%).

(5) Preparation of Compound 23

Compound 9D (20.0 g, 26.19 mmol) and Reagent 5 (4.1 g, 26.19 mmol) were put into 300 ml of tetrahydrofuran under a nitrogen atmosphere, and the resulting mixture was stirred and refluxed. Thereafter, potassium carbonate (10.9 g, 78.58 mmol) was dissolved in 50 ml of water, the resulting solution was introduced into the mixture, the resulting mixture was sufficiently stirred, and then tetrakis-triphenyl-phosphinopalladium (0.9 g, 0.79 mmol) was introduced thereinto. After the reaction for 12 hours, the temperature of the product was lowered to normal temperature and a produced solid was filtered. After the filtration, the solid was washed with 100 ml of tetrahydrofuran, 500 ml of ethyl acetate, 500 ml of water, and 300 ml of ethanol. Thereafter, the material was extracted by using chloroform and water, and then Compound (10.5 g, 60%) was prepared through recrystallization.

MS: $[M+H]^+$=666

EXAMPLES

Experimental Example 1-1

A glass substrate (Corning 7059 glass) thinly coated with ITO (indium tin oxide) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on the transparent ITO electrode, which was thus prepared, thereby forming a hole injection layer. HT1 (400 Å), which is a material transporting holes, was vacuum deposited thereon, and then compounds of a host H1 and a dopant D1 were vacuum deposited as a light emitting layer to have a thickness of 300 Å. Compound 1 prepared in Synthesis Example 1 and LiQ (lithium quinolate) were vacuum deposited at a weight ratio of 1:1 on the light emitting layer, thereby forming an electron injection and transport layer having a thickness of 350 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

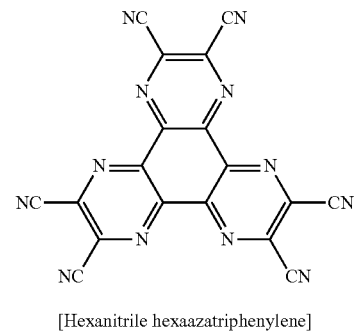

[Hexanitrile hexaazatriphenylene]

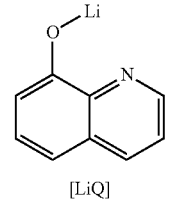

[LiQ]

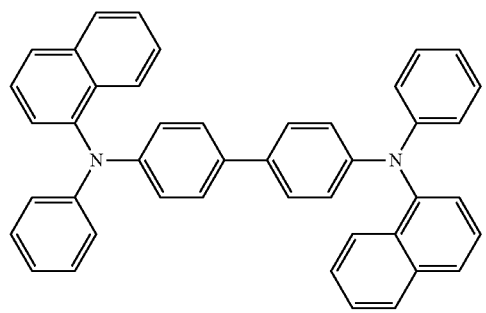

[HT1]

[H1]

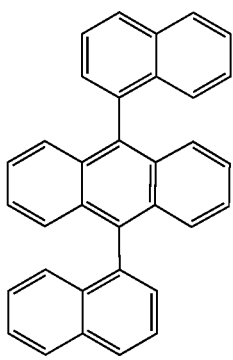

[D1]

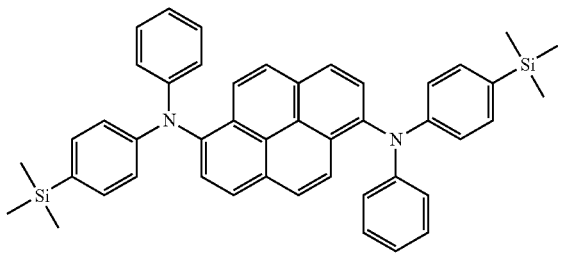

Experimental Example 1-2

An experiment was performed in the same manner as in Experimental Example 1-1, except that as the electron transport layer, Compound 2 was used instead of Compound 1.

Experimental Example 1-3

An experiment was performed in the same manner as in Experimental Example 1-1, except that as the electron transport layer, Compound 3 was used instead of Compound 1.

Experimental Example 1-4

An experiment was performed in the same manner as in Experimental Example 1-1, except that as the electron transport layer, Compound 4 was used instead of Compound 1.

Experimental Example 1-5

An experiment was performed in the same manner as in Experimental Example 1-1, except that as the electron transport layer, Compound 7 was used instead of Compound 1.

Experimental Example 1-6

An experiment was performed in the same manner as in Experimental Example 1-1, except that as the electron transport layer, Compound 8 was used instead of Compound 1.

Experimental Example 1-7

An experiment was performed in the same manner as in Experimental Example 1-1, except that as the electron transport layer, Compound 9 was used instead of Compound 1.

Experimental Example 1-8

An experiment was performed in the same manner as in Experimental Example 1-1, except that as the electron transport layer, Compound 12 was used instead of Compound 1.

Experimental Example 1-9

An experiment was performed in the same manner as in Experimental Example 1-1, except that as the electron transport layer, Compound 23 was used instead of Compound 1.

Comparative Example 1

An organic light emitting device was manufactured in the same manner as in Experimental Example 1-1, except that a compound of the following ET1 was used instead of Compound 1 in Experimental Example 1-1.

[ET1]

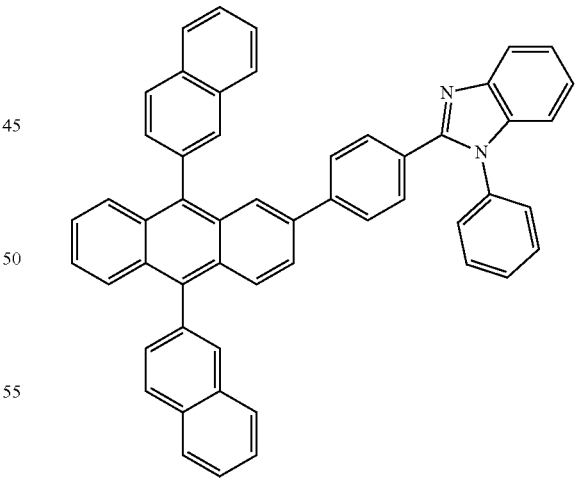

Comparative Example 2

An organic light emitting device was manufactured in the same manner as in Experimental Example 1-1, except that a compound of the following ET2 was used instead of Compound 1 in Experimental Example 1-1.

[ET2]

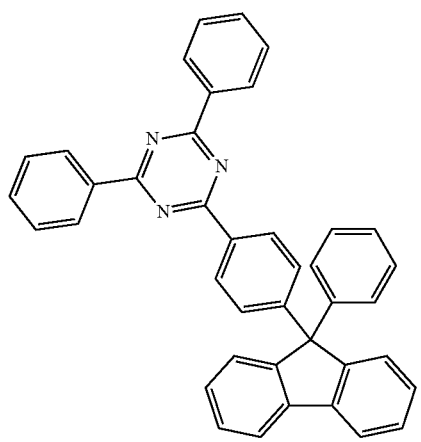

Comparative Example 3

An organic light emitting device was manufactured in the same manner as in Experimental Example 1-1, except that a compound of the following ET4 was used instead of Compound 1 in Experimental Example 1-1.

[ET4]

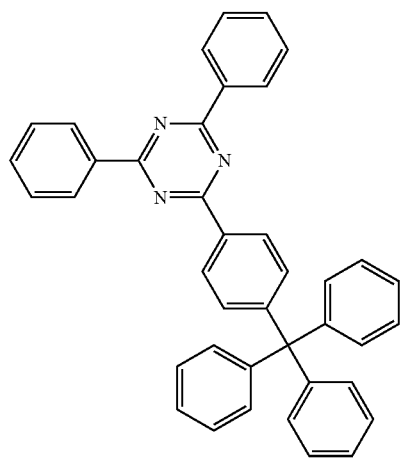

For the organic light emitting devices manufactured by using each compound as the electron transporting layer material as in Experimental Examples 1-1 to 1-9 and Comparative Examples 1 to 3, the driving voltage and the light emitting efficiency were measured at a current density of 10 mA/cm$^2$, and a time ($LT_{98}$) for reaching a 98% value compared to the initial luminance was measured at a current density of 20 mA/cm$^2$. The results are shown in the following Table 1.

TABLE 1

| Experimental Example @10 mA/cm$^2$ | Compound | Voltage (V) | Current efficiency (cd/A) | Color coordinate (x, y) | LT 95% (hr) @20 mA/cm$^2$ |
|---|---|---|---|---|---|
| Experimental Example 1-1 | Compound 1 | 4.23 | 5.59 | (0.141, 0.152) | 42 |
| Experimental Example 1-2 | Compound 2 | 4.24 | 5.66 | (0.140, 0.153) | 42 |
| Experimental Example 1-3 | Compound 3 | 4.35 | 5.45 | (0.140, 0.151) | 51 |
| Experimental Example 1-4 | Compound 4 | 4.24 | 5.49 | (0.142, 0.149) | 65 |
| Experimental Example 1-5 | Compound 7 | 4.22 | 5.88 | (0.143, 0.153) | 35 |
| Experimental Example 1-6 | Compound 8 | 4.38 | 5.25 | (0.144, 0.150) | 90 |
| Experimental Example 1-7 | Compound 9 | 4.22 | 6.10 | (0.140, 0.150) | 29 |
| Experimental Example 1-8 | Compound 12 | 4.18 | 6.24 | (0.142, 0.152) | 28 |
| Experimental Example 1-9 | Compound 23 | 4.24 | 5.49 | (0.143, 0.153) | 60 |
| Comparative Example 1 | ET1 | 4.03 | 5.16 | (0.134, 0.141) | 29.5 |
| Comparative Example 2 | ET2 | 4.00 | 6.21 | (0.139, 0.148) | 15 |
| Comparative Example 3 | ET4 | 4.01 | 6.18 | (0.134, 0.148) | 17 |

As can be seen in Table 1, it can be seen that an organic light emitting device manufactured using the compound of the present specification as an electron transport layer material exhibits excellent characteristics in terms of efficiency and stability when compared with the case of using the materials in Comparative Examples 1 to 3.

Although the preferred exemplary embodiments of the present invention have been described above, the present invention is not limited thereto, and various modifications can be made and carried out within the scope of the claims and the detailed description of the invention, and also belong to the scope of the invention.

The invention claimed is:

1. A compound represented by the following Chemical Formula 1:

[Chemical Formula 1]

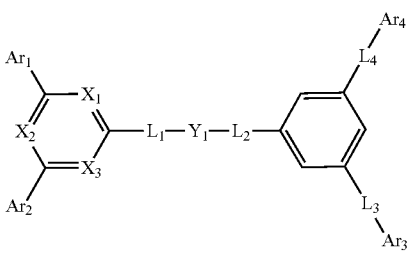

in Chemical Formula 1,
$X_1$ to $X_3$ are the same as or different from each other, and are each independently N or $CR_1$,
at least one of $X_1$ to $X_3$ is N,
$R_1$ is hydrogen or deuterium,
$Y_1$ is a substituted or unsubstituted naphthylene group,
$L_1$ to $L_4$ are the same as or different from each other, and are each independently a direct bond; a substituted or unsubstituted arylene group; a substituted or unsubstituted heteroarylene group; or a substituted or unsubstituted divalent arylamine group,
$Ar_1$ and $Ar_2$ are the same as or different from each other, and are each independently hydrogen; deuterium; a halogen group; an amino group; a nitrile group; a nitro group; a substituted or unsubstituted cycloalkyl group; a substituted or unsubstituted aryl group; or a substituted or unsubstituted heteroaryl group, and at least one of $Ar_1$ and $Ar_2$ is not hydrogen or deuterium, and $Ar_3$ and $Ar_4$ are the same as or different from each other, and are each independently a substituted or unsubstituted pyridyl group.

2. The compound of claim 1, wherein the compound of Chemical Formula 1 is represented by the following Chemical Formula 2:

[Chemical Formula 2]

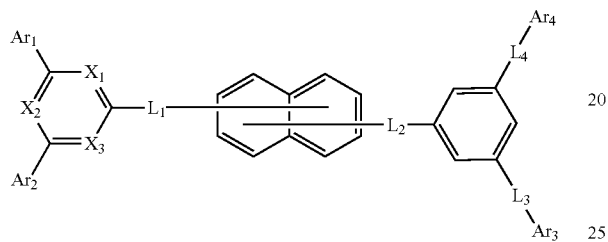

in Chemical Formula 2, the definitions of $X_1$ to $X_3$, $Ar_1$ to $Ar_4$, and $L_1$ to $L_4$ are the same as those in Chemical Formula 1.

3. The compound of claim 1, wherein the compound of Chemical Formula 1 is represented by the following Chemical Formula 3 or 4:

[Chemical Formula 3]

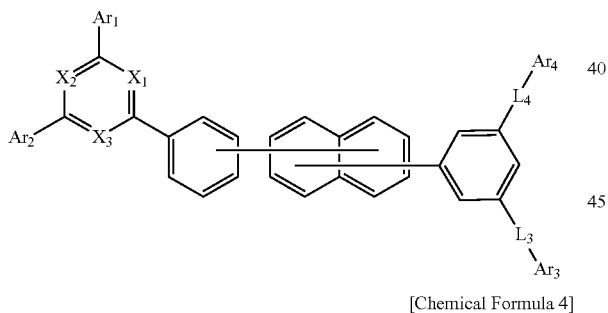

[Chemical Formula 4]

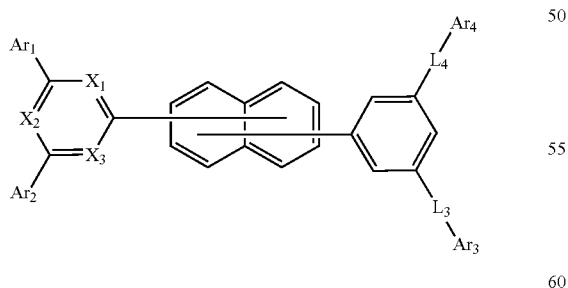

in Chemical Formulae 3 and 4, the definitions of $X_1$ to $X_3$, $Ar_1$ to $Ar_4$, $L_3$, and $L_4$ are the same as those in Chemical Formula 1.

4. The compound of claim 1, wherein the compound of Chemical Formula 1 is represented by any one of the following Chemical Formulae 5 to 14:

[Chemical Formula 5]

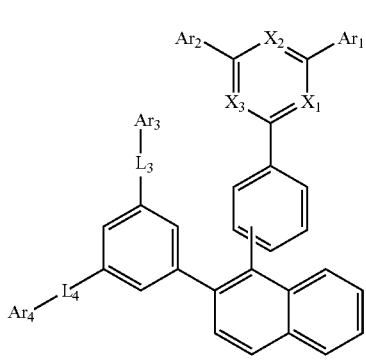

[Chemical Formula 6]

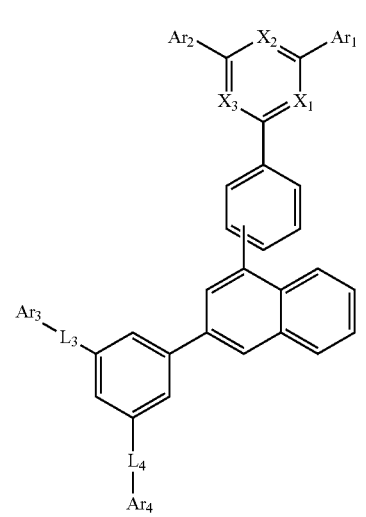

[Chemical Formula 7]

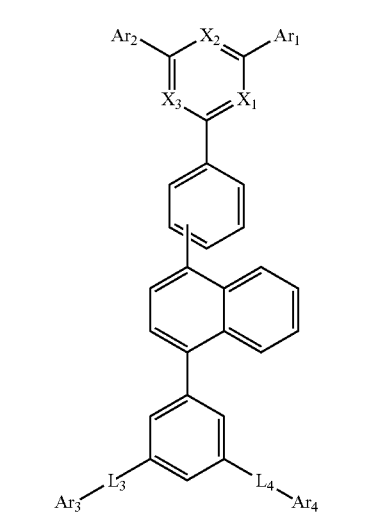

[Chemical Formula 8]

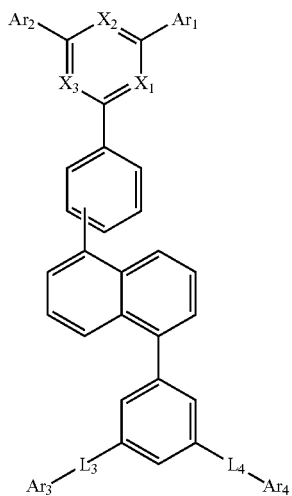

[Chemical Formula 11]

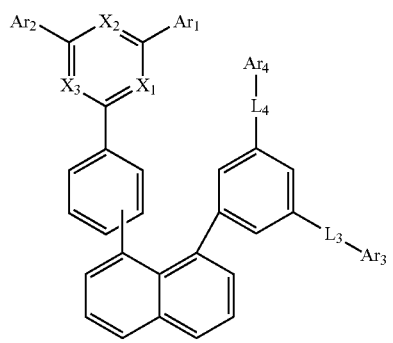

[Chemical Formula 12]

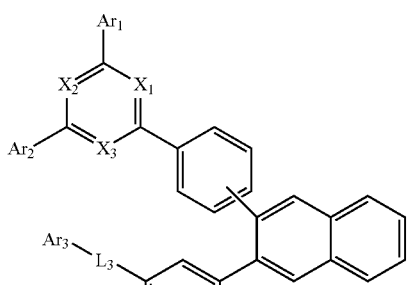

[Chemical Formula 9]

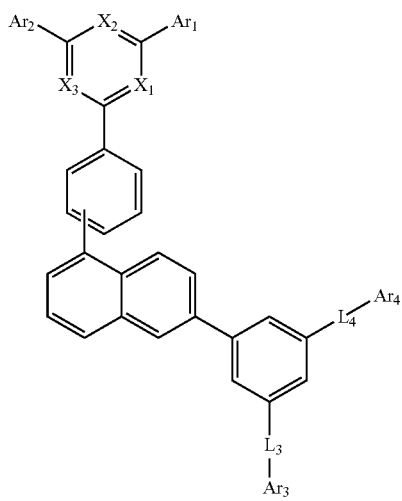

[Chemical Formula 13]

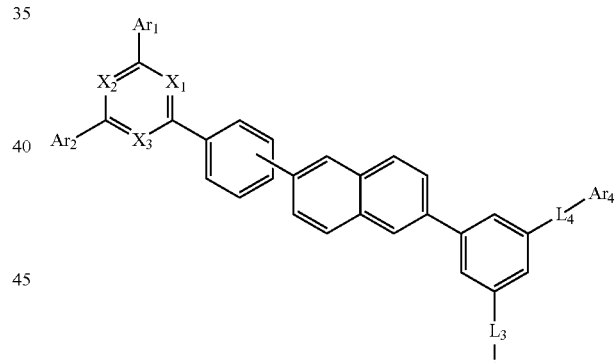

[Chemical Formula 10]

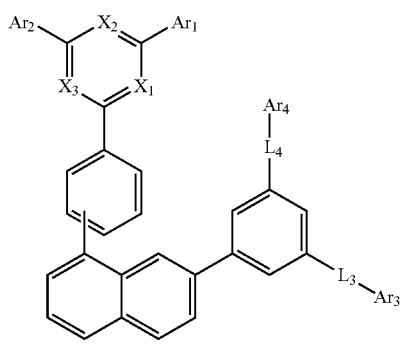

[Chemical Formula 14]

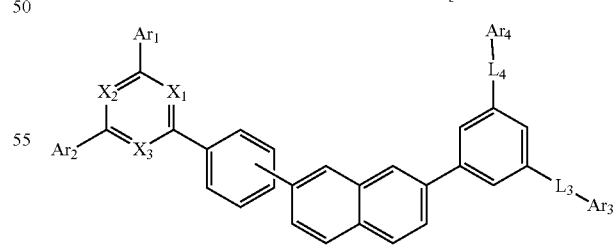

in Chemical Formulae 5 to 14, the definitions of $X_1$ to $X_3$, $Ar_1$ to $Ar_4$, $L_3$, and $L_4$ are the same as those in Chemical Formula 1.

5. The compound of claim 1, wherein the compound of Chemical Formula 1 is represented by any one of the following Chemical Formulae 15 to 24:

[Chemical Formula 15]
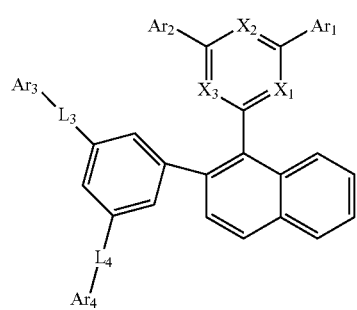
[Chemical Formula 16]
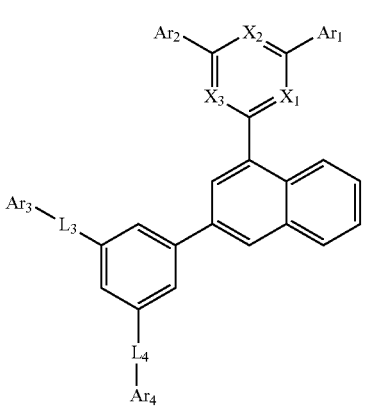
[Chemical Formula 17]
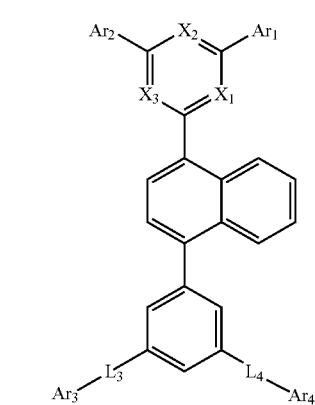
[Chemical Formula 18]
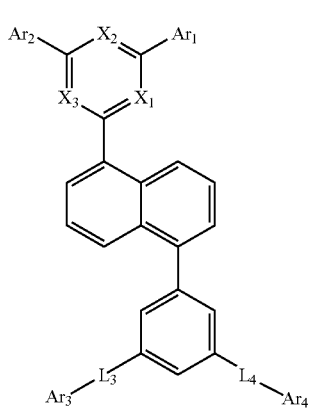
[Chemical Formula 19]
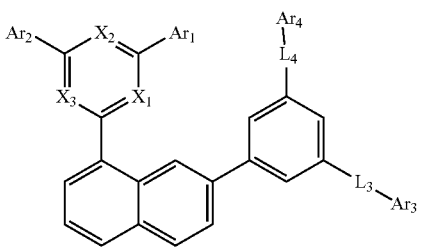
[Chemical Formula 20]
[Chemical Formula 21]
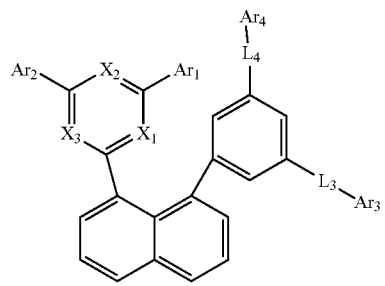

[Chemical Formula 22]

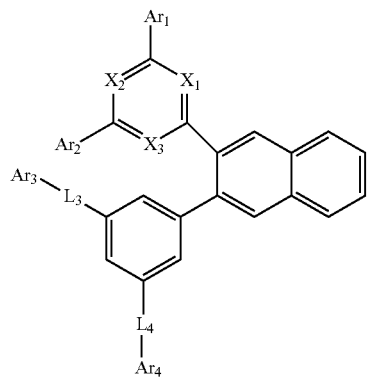

[Chemical Formula 23]

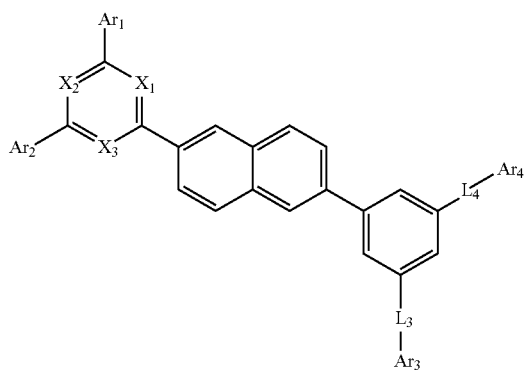

[Chemical Formula 24]

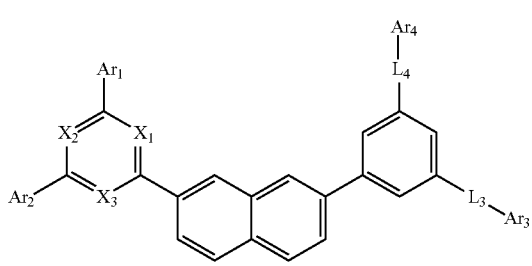

in Chemical Formulae 15 to 24, the definitions of $X_1$ to $X_3$, $Ar_1$ to $Ar_4$, $L_3$, and $L_4$ are the same as those in Chemical Formula 1.

6. The compound of claim 1, wherein $Ar_a$ and $Ar_4$ are the same as or different from each other, and are each independently

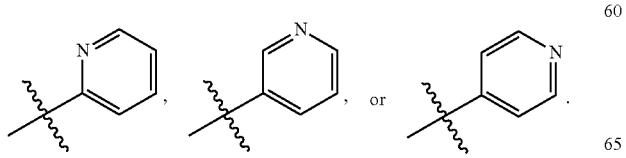

7. The compound of claim 1, wherein the compound of Chemical Formula 1 is any one selected from the following compounds:

[Compound 1]

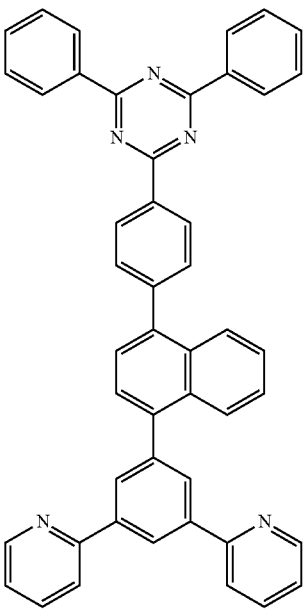

[Compound 2]

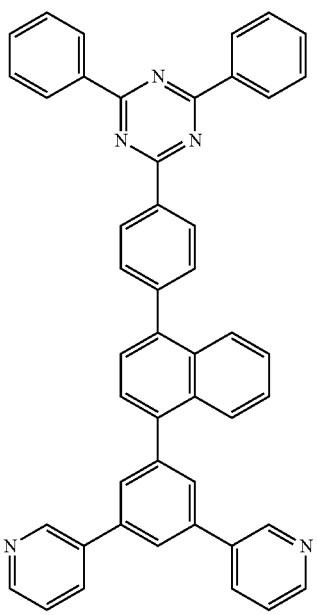

[Compound 3]
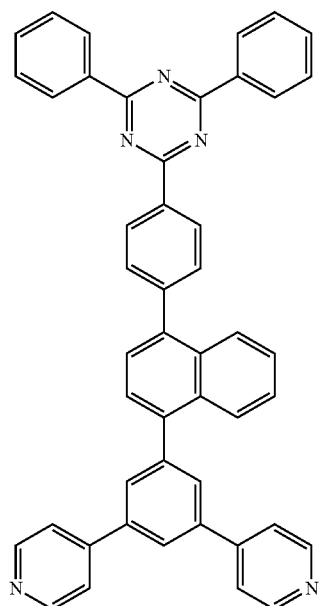
[Compound 4]
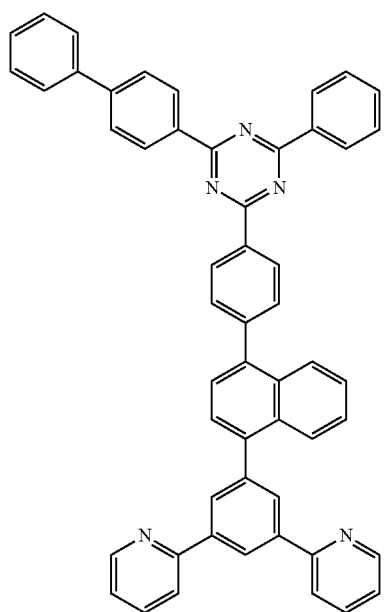
[Compound 5]
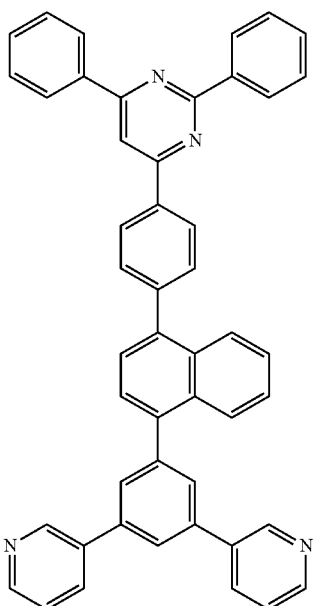
[Compound 6]
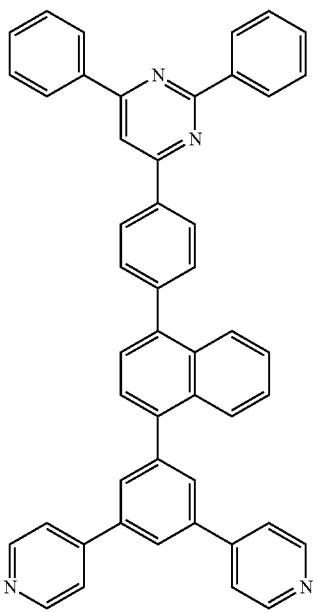

[Compound 7]
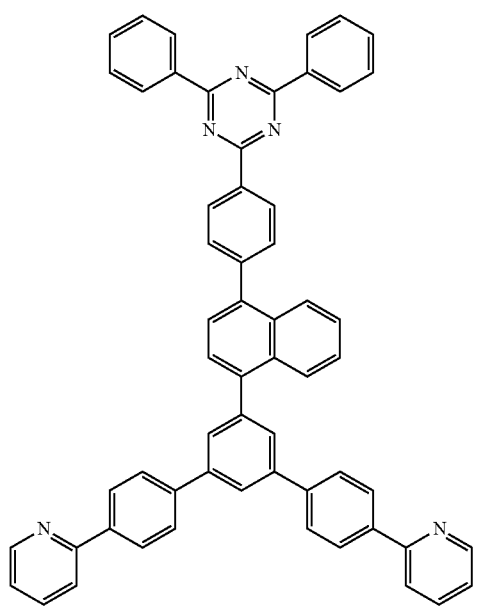
[Compound 9]
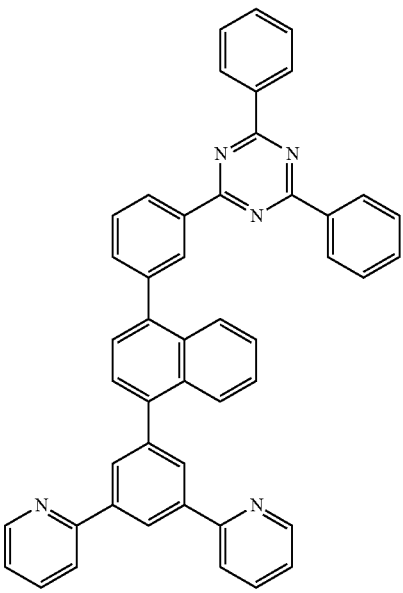
[Compound 8]
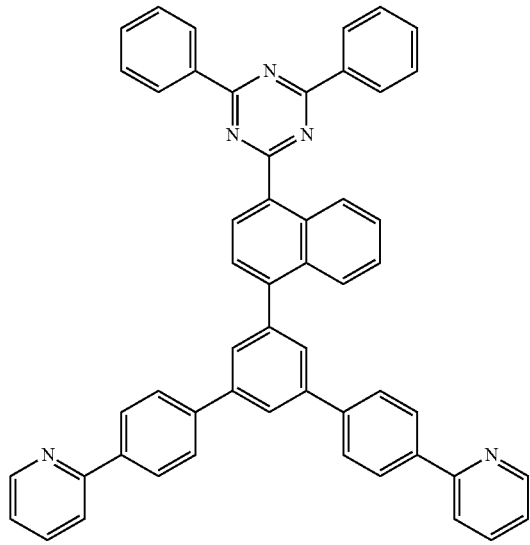
[Compound 10]
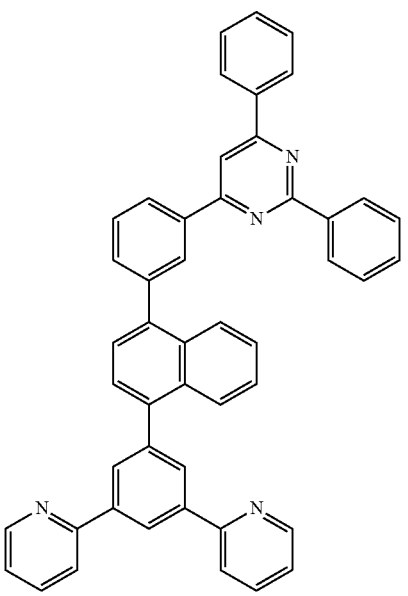

[Compound 11]
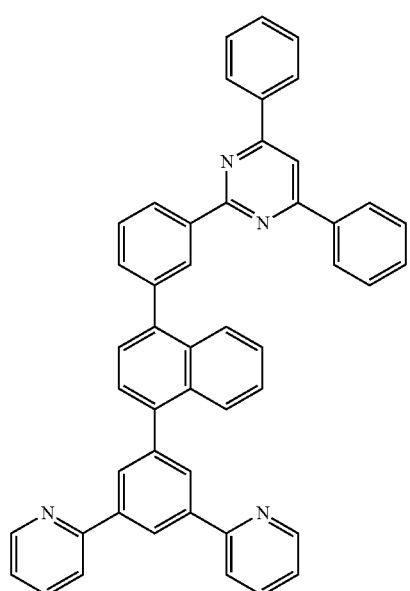
[Compound 14]
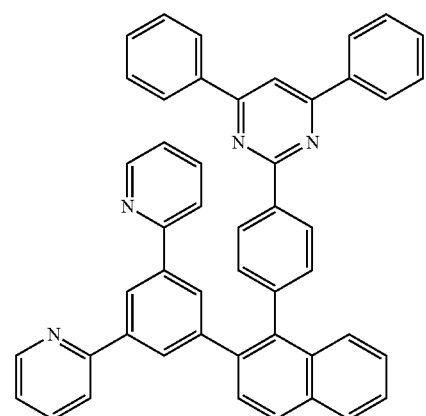
[Compound 12]
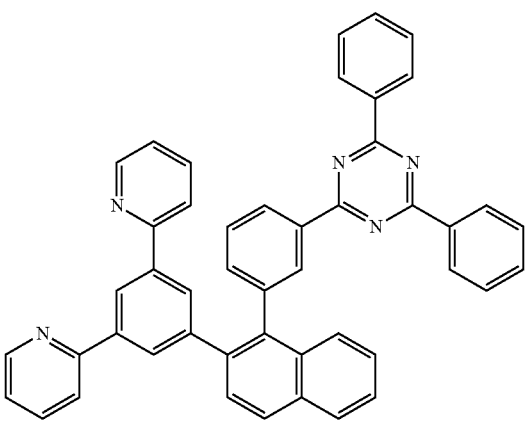
[Compound 15]
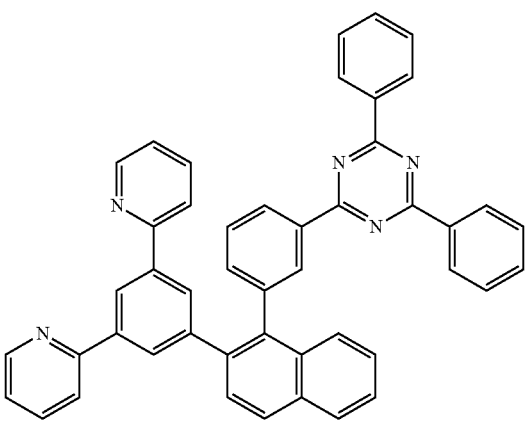
[Compound 13]
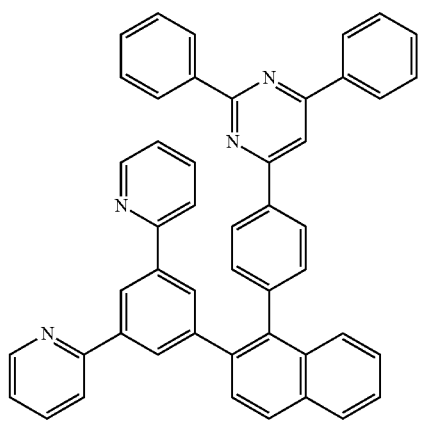
[Compound 16]
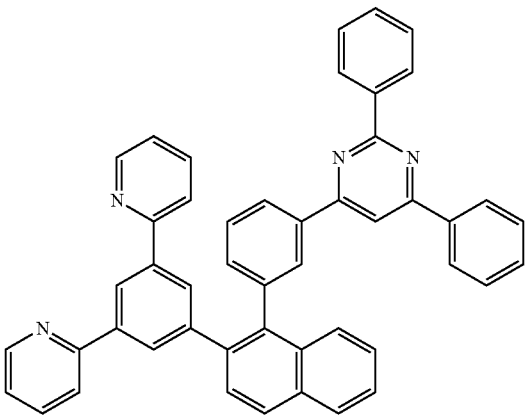

[Compound 17]
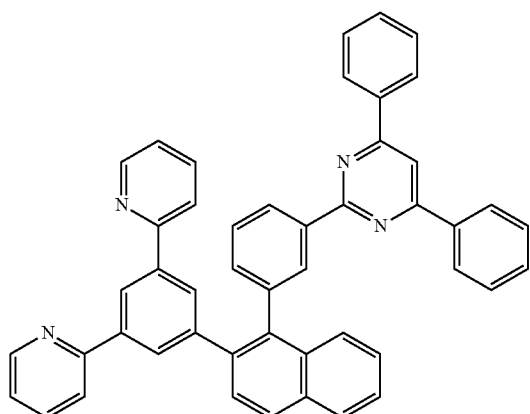
[Compound 19]
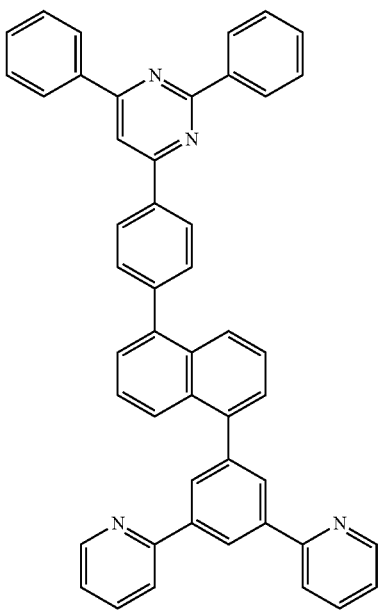
[Compound 18]
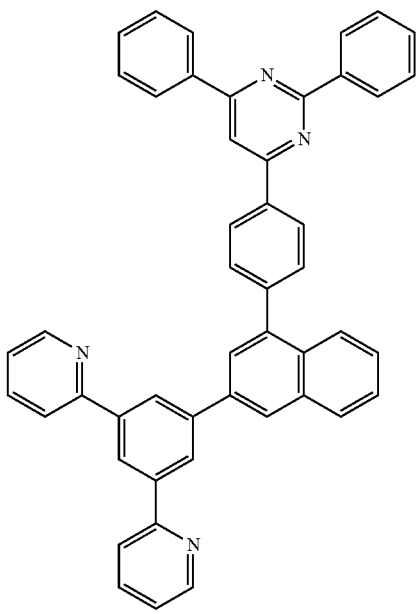
[Compound 20]
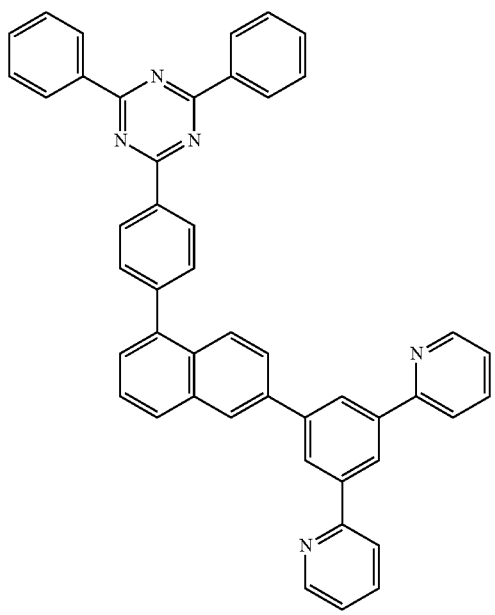

[Compound 21]
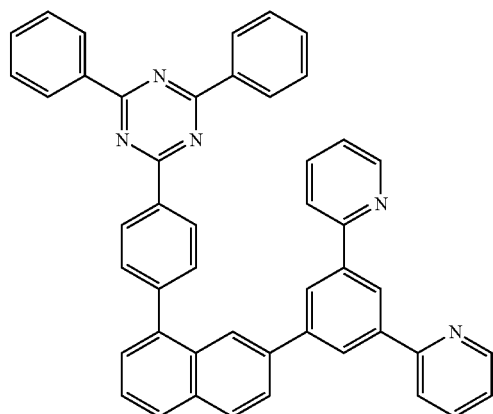
[Compound 22]
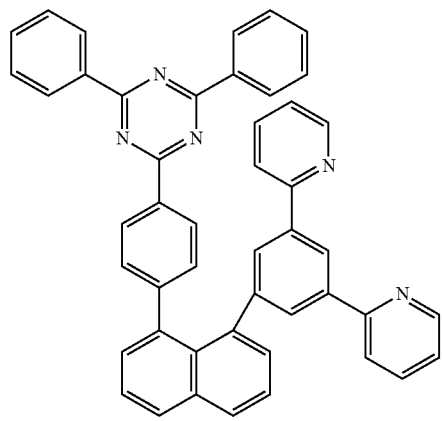
[Compound 23]
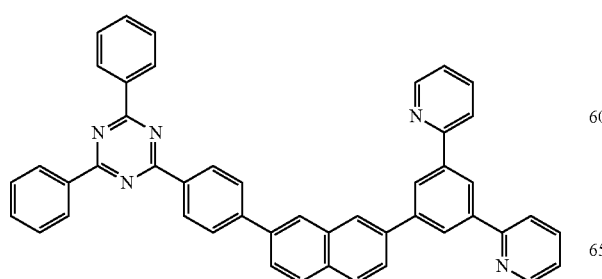
[Compound 24]
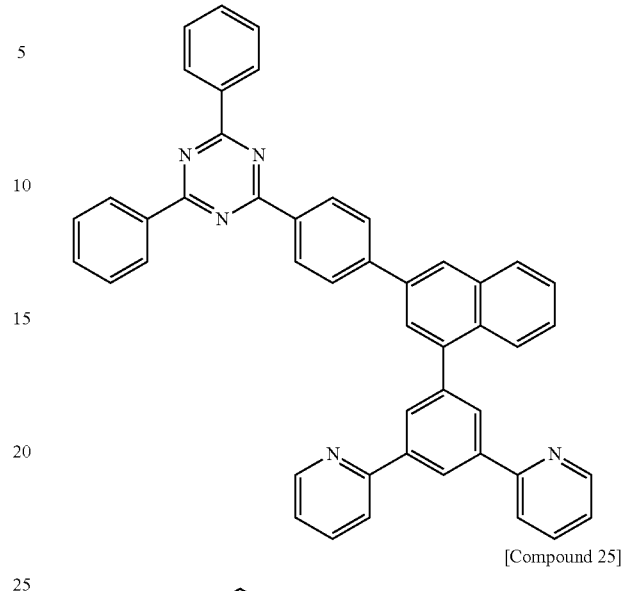
[Compound 25]
[Compound 26]
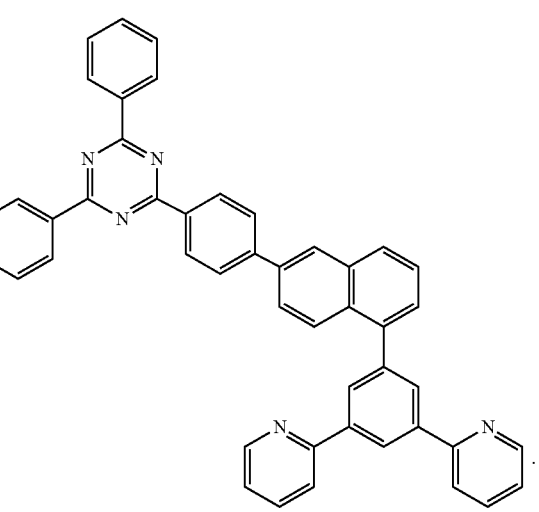

8. An organic light emitting device comprising:
a first electrode;
a second electrode; and
one or more organic material layers disposed between the first electrode and the second electrode,
wherein one or more layers of the organic material layers comprise the compound of claim 1.

9. The organic light emitting device of claim 8, wherein the organic material layer comprises at least one layer of an electron transport layer; an electron injection layer; and a layer which transports and injects electrons simultaneously, and at least one layer of the layers comprises the compound.

10. The organic light emitting device of claim 8, wherein the organic material layer comprises an electron transport and hole blocking layer, and the electron transport and hole blocking layer comprises the compound.

11. The organic light emitting device of claim 8, wherein the organic material layer comprises a light emitting layer, and the light emitting layer comprises the compound as a host of the light emitting layer.

12. The organic light emitting device of claim 8, wherein the organic material layer comprises at least one layer of a hole injection layer; a hole transport layer; and a layer which injects and transports holes simultaneously, and at least one layer of the layers comprises the compound.

13. The organic light emitting device of claim 8, wherein the organic material layer comprises the compound as a host, and comprises another organic compound, a metal, or a metal compound as a dopant.

14. The organic light emitting device of claim 8, wherein the organic material layer comprises a light emitting layer, and the light emitting layer comprises a compound of the following Chemical Formula A-1:

[Chemical Formula A-1]

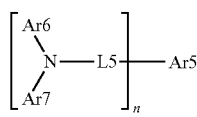

in Chemical Formula A-1,
n is an integer of 1 or more,
Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L5 is a direct bond; a substituted or unsubstituted arylene group; or a substituted or unsubstituted heteroarylene group,
Ar6 and Ar7 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heterocyclic group, or optionally combine with each other to form a substituted or unsubstituted ring, and
when n is 2 or more, two or more structures in the parenthesis are the same as or different from each other.

15. The organic light emitting device of claim 14, wherein L5 is a direct bond,
Ar5 is a divalent pyrene group, and
Ar6 and Ar7 are the same as or different from each other, and are each independently an aryl group which is unsubstituted or substituted with a silyl group substituted with an alkyl group, and n is 2.

16. The organic light emitting device of claim 14, wherein the light emitting layer comprises a compound represented by the following Chemical Formula A-2:

[Chemical Formula A-2]

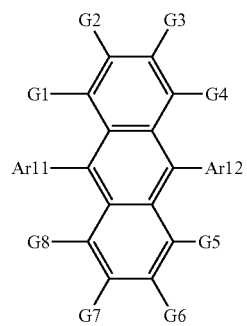

in Chemical Formula A-2,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

17. The organic light emitting device of claim 8, wherein the organic material layer comprises a light emitting layer, and the light emitting layer comprises a compound represented by the following Chemical Formula A-2:

[Chemical Formula A-2]

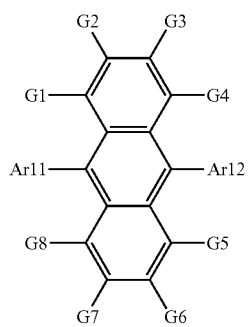

in Chemical Formula A-2,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

18. The organic light emitting device of claim 17, wherein Ar11 and Ar12 are a 1-naphthyl group, and G1 to G8 are hydrogen.

* * * * *